United States Patent
Tarkanic et al.

[11] Patent Number: 6,075,609
[45] Date of Patent: Jun. 13, 2000

[54] APPARATUS AND METHODS FOR IMPROVING FLUORESCENCE DETECTORS

[75] Inventors: Stephen Tarkanic, Houston; James S. Wreyford, Spring; Abige Davie Harkins, Houston, all of Tex.

[73] Assignee: Antek Industrial Instruments, Inc., Marble Falls, Tex.

[21] Appl. No.: 09/048,949

[22] Filed: Mar. 26, 1998

[51] Int. Cl.[7] .......................... G01N 21/25; G01N 21/64
[52] U.S. Cl. ...................... 356/417; 356/246; 250/461.1
[58] Field of Search .................................. 356/246, 417, 356/317; 250/461.1

[56] References Cited

U.S. PATENT DOCUMENTS

| | | | |
|---|---|---|---|
| 4,070,155 | 1/1978 | Fraim | 23/230 |
| 4,575,424 | 3/1986 | Allington et al. | 356/246 |
| 4,765,373 | 8/1988 | Munroe | 137/890 |
| 4,952,376 | 8/1990 | Peterson | 422/186.3 |
| 5,422,712 | 6/1995 | Ogino | 356/417 |
| 5,557,415 | 9/1996 | Nielsen et al. | 356/417 |

*Primary Examiner*—Frank G. Font
*Assistant Examiner*—Zandra V. Smith
*Attorney, Agent, or Firm*—Robert W Strozier

[57] ABSTRACT

A method and apparatus are disclosed for the improving the sensitivity of fluorescent detectors, especially UV fluorescent detectors using a light reaction cell including a reaction chamber having an optically smooth, highly reflective interior surface. The chamber can also include an insert that imparts either or both optically smooth and high reflectivity to the chamber. Increased interior surface smoothness and reflectivity significantly improves sensitivity and detection limits making ppb measurements routine.

24 Claims, 30 Drawing Sheets

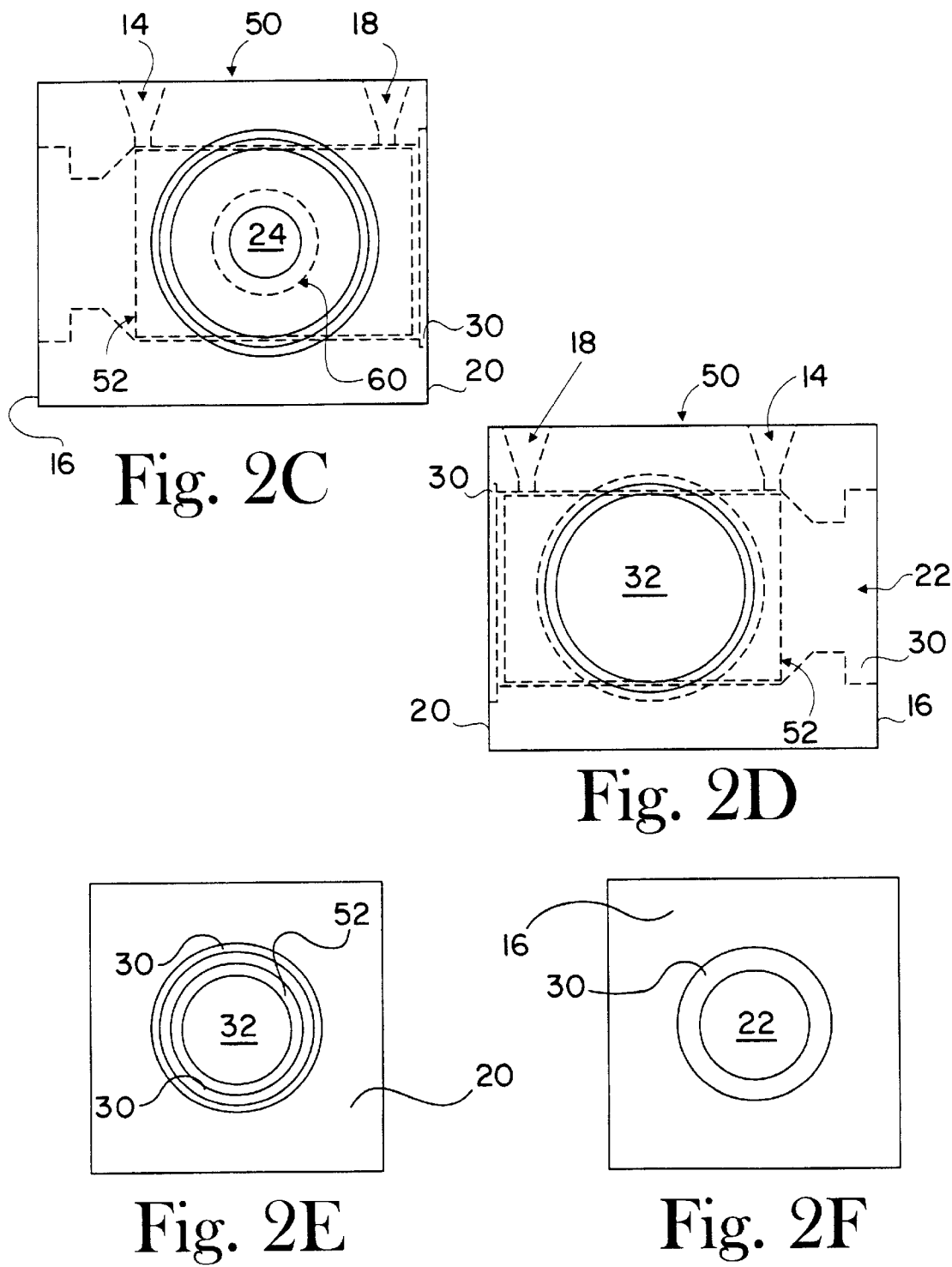

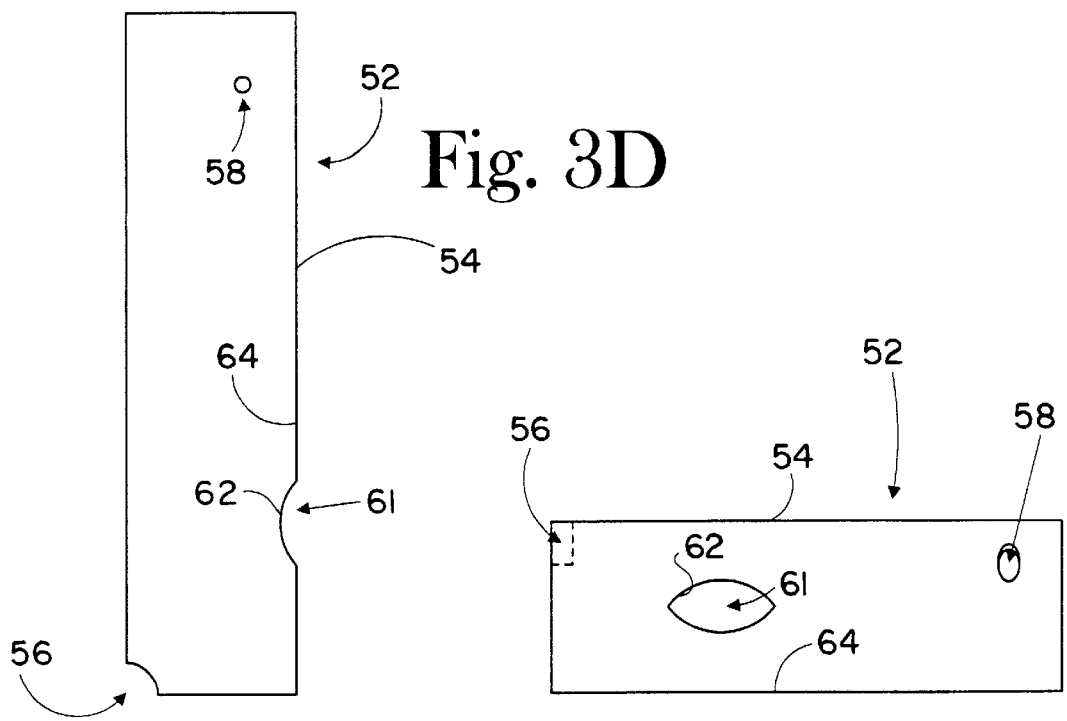
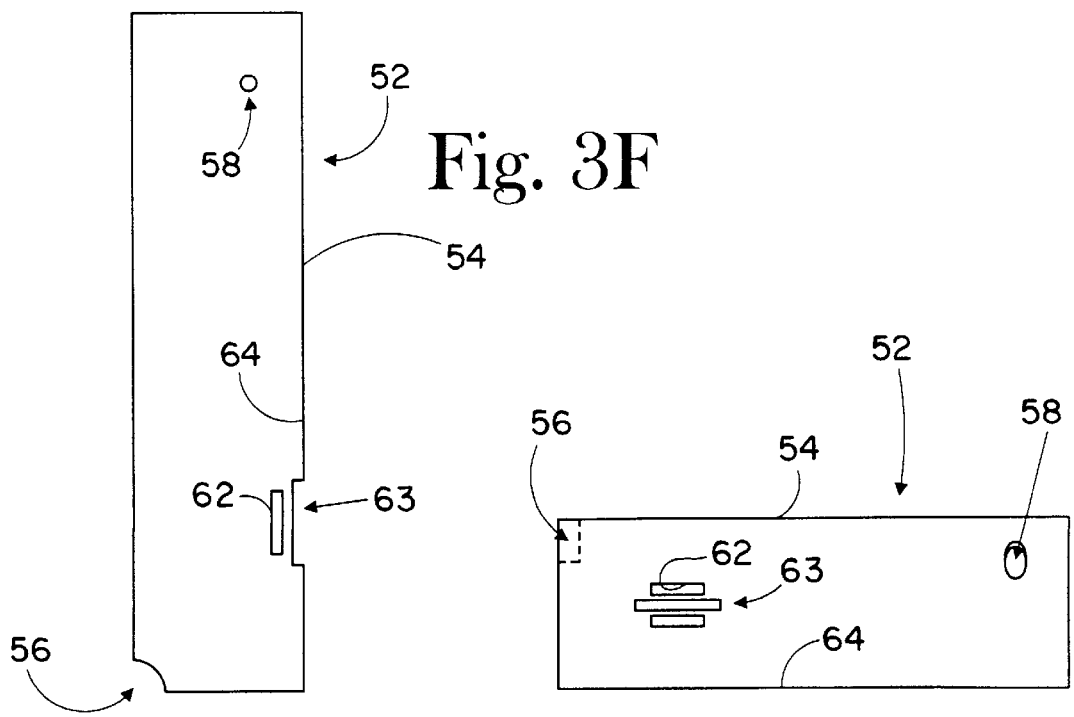

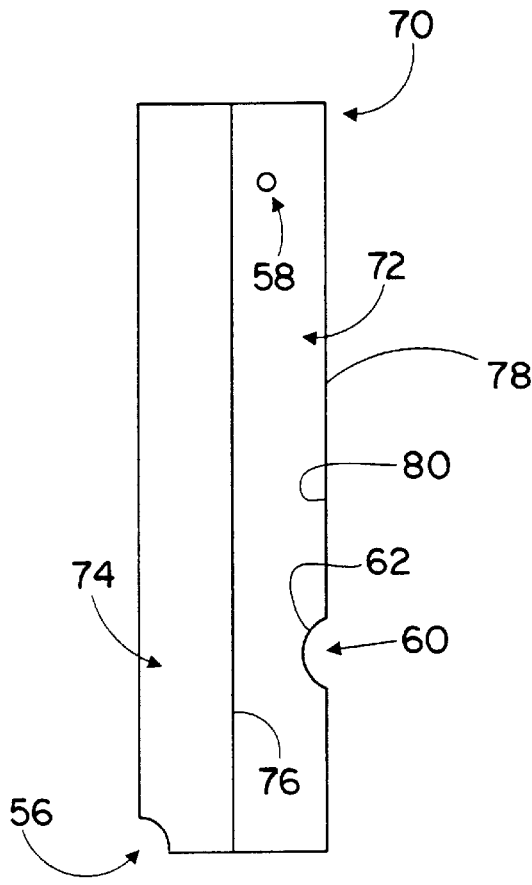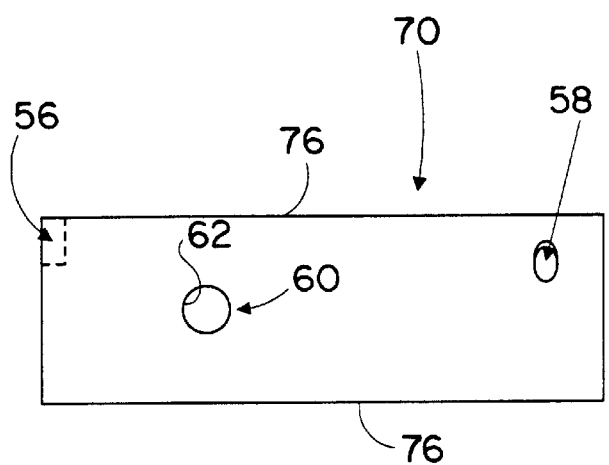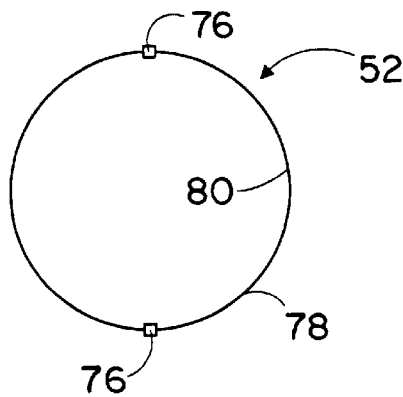
Fig. 4A  Fig. 4B
Fig. 4C

APPARATUS AND METHODS FOR IMPROVING FLUORESCENCE DETECTORS

BACKGROUND OF THE INVENTION

1. Field of the Invention

This invention relates to methods and apparatus for improving the sensitivity and detection limits of UV fluorescence detectors.

More particularly, the present invention relates to methods and apparatus for improving the sensitivity and detection limits of fluorescence detectors which include a reaction cell having optical smooth and highly reflective internal surfaces that are preferably composed of a material that does not react with the sample or photo-excited components in the sample being analyzed.

2. Description of the Related Art

Fluorescence detectors such as UV fluorescent detectors generally include a reaction chamber where a sample to be analyzed is exposed to light from a source. The light is absorbed by certain components in the sample that then fluoresce. The fluorescence is measured by a detector such as a photomultiplier tube and the detector output is converted into a readable output.

One major deficiency of current light reaction chambers is that signal to noise ratios prevent reliable and reproducible determination of trace components much below about 1 ppm. Thus, there is a need in the art for an efficient, cost effective procedure for increasing the sensitivity and detection limit of fluorescent detectors.

SUMMARY OF THE INVENTION

This invention provides a light reaction cell for improving the sensitivity and detection limits of fluorescence spectroscopy including UV fluorescent spectroscopy where the cell includes a photo-reaction chamber having interior surfaces that are reflective to a desired light frequency (wavelength) range and preferably highly reflective and optically smooth.

The cell generally includes a sample entrance port and a sample exit port. The cell generally also includes a light input port in optical communication with a light source assembly. The cell further generally includes a fluorescent light detector port in optical communication with a detector/analyzer assembly. The cell further generally includes a reaction chamber having interior surfaces or a reaction chamber insert. Generally, the interior surfaces are reflective to a desired frequency range of light such as the UV region of the electromagnetic spectrum associated with the compound or compounds to be analyzed. Preferably, the interior surfaces are highly reflective and highly polished or optically smooth. One part of the highly reflective interior surfaces are constructed to reflect fluorescent light emitted away from the detector port towards the reflector port, increasing the fluorescent light into the detector/analyzer assembly. The fluorescent light reflective portion of the interior surfaces can also be constructed to focus fluorescent light emitted away from the detector port into the port. Another part of the highly reflective interior surfaces can be constructed to reflect the excitation light passing through the chamber back into the chamber increasing the excitation light concentration in the chamber. The excitation light reflective part of the interior surfaces can also be constructed to reflect and focus the excitation light into a central region of the chamber. Highly reflective and optically smooth surfaces increase a signal-to-noise ratio of the detector and improve both sensitive and detection limit of the detector.

The present invention also provides a fluorescent instrument which includes a sample delivery system, a light reaction cell as described above, a light source, and a fluorescent detector/analyzer system.

The present invention further provides a method for improving sensitivity and detection limits of fluorescent detectors and instruments by contacting a sample with light in a reaction cell as described above.

DESCRIPTION OF THE DRAWINGS

The invention can be better understood with reference to the following detailed description together with the appended drawings where like elements are numbered the same:

FIG. 1B is a top view of the reaction cell of FIG. 1a;

FIG. 1C is a front view of the reaction cell of FIG. 1a;

FIG. 1D is a right end view of the reaction cell of FIG. 1a;

FIG. 1E is a left end view of the reaction cell of FIG. 1a;

FIG. 1F is an expanded view of the interior surface of the cell of FIG. 1a;

FIG. 2B is a top view of the reaction cell of FIG. 2a;

FIG. 2C is a front view of the reaction cell of FIG. 2a;

FIG. 2D is a rear view of the reaction cell of FIG. 2a;

FIG. 2E is a right end view of the reaction cell of FIG. 2a;

FIG. 2F is a left end view of the reaction cell of FIG. 2a;

FIG. 3B is a second side view of the insert of FIG. 3a;

FIG. 3C is a end view of the insert of FIG. 3a;

FIG. 3D is a first side view of one embodiment of a reaction cell insert of the present invention;

FIG. 3E is a second side view of the insert of FIG. 3a;

FIG. 3F is a first side view of one embodiment of a reaction cell insert of the present invention;

FIG. 3G is a second side view of the insert of FIG. 3a;

FIG. 4A is a first side view of a second embodiment of a reaction cell insert of the present invention;

FIG. 4B is a second side view of the insert of FIG. 4a;

FIG. 4C is a end view of the insert of FIG. 4a;

FIG. 5A is a side view of a second embodiment of a reaction cell insert of the present invention;

FIG. 5B is a side view of a variation of the insert of FIG. 5a;

FIG. 5C is a end view of the insert of FIG. 5a;

DESCRIPTION OF THE PREFERRED EMBODIMENTS

Figure 1A:
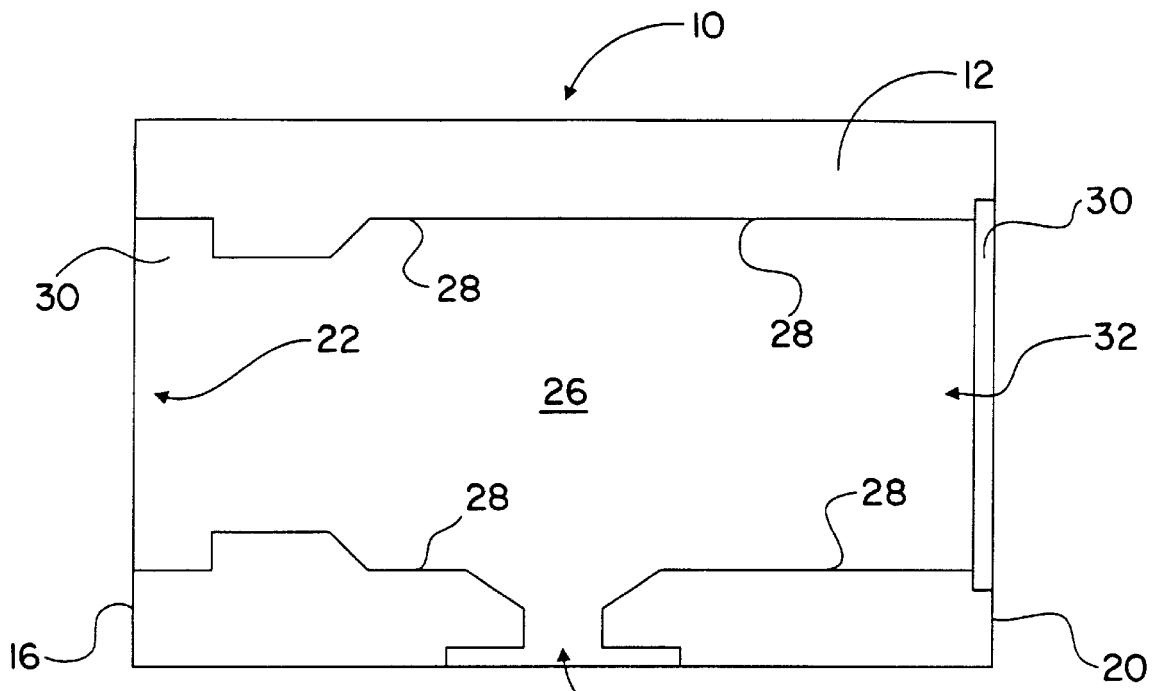
FIG. 1A is a cross-sectional top view of one embodiment of a reaction cell of the present invention.
Figure 1B:
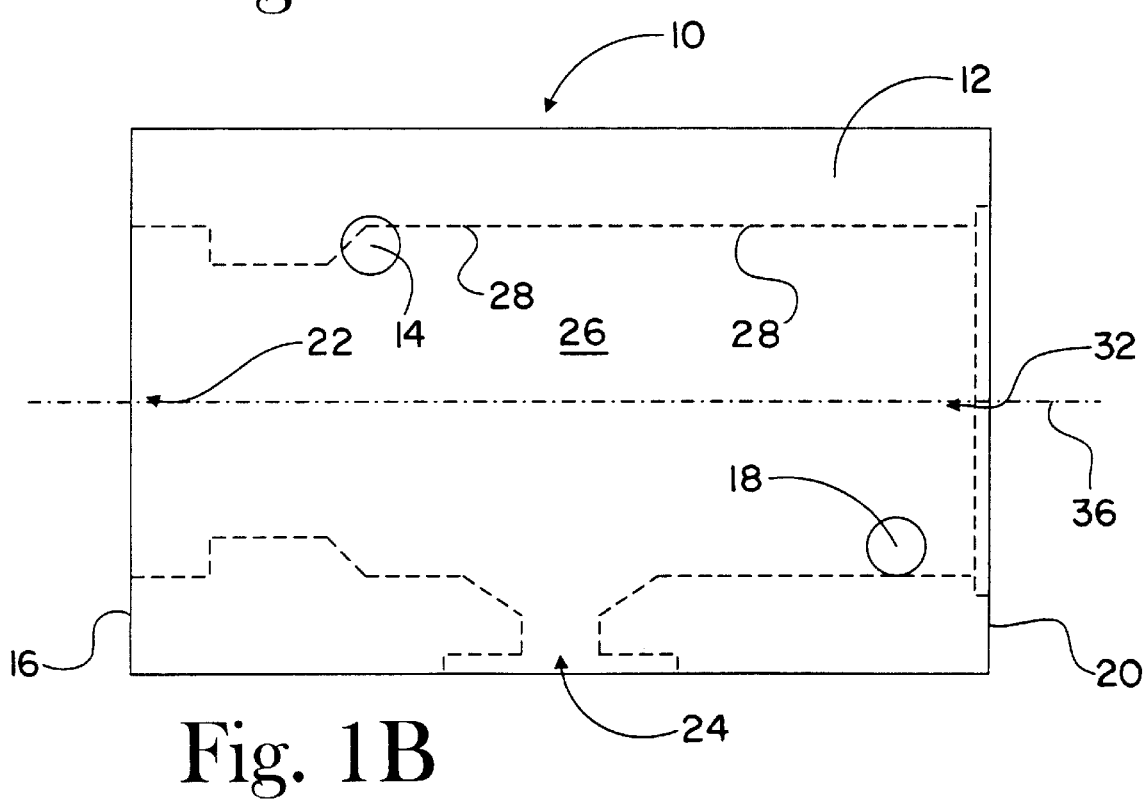
Figure 1C:
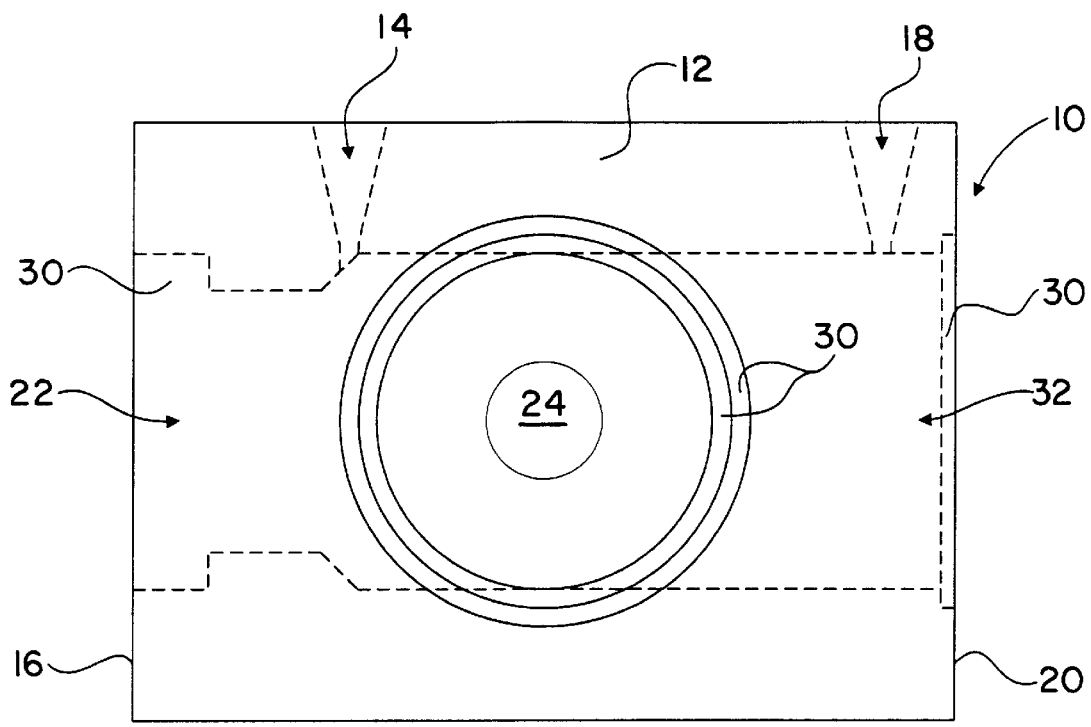
Figures 1D, 1E:
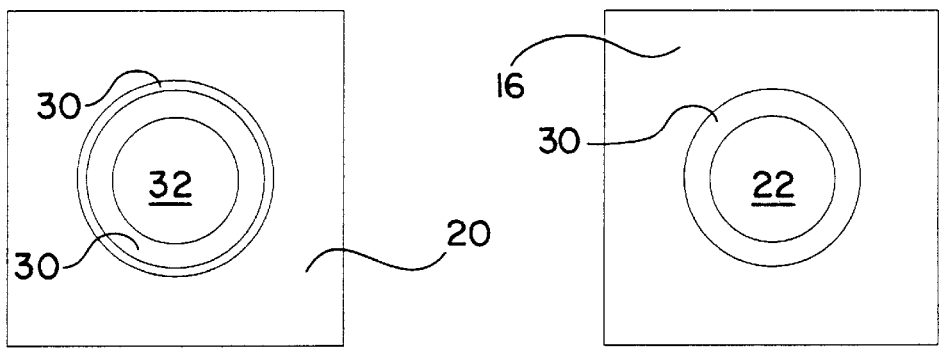

The inventors have found that an apparatus can be constructed that is capable of improving the sensitivity and the detection limit of fluorescence instruments such as UV fluorescent instruments. The improvement in sensitivity and detection limit was achieved by changing the nature of interior surfaces of a light reaction chamber of a reaction cell associated with a fluorescence instrument.

Prior art light reaction chambers generally had interior surfaces that were coated black and roughly textured. The inventors have found that highly reflective, and preferably highly polished or optically smooth, interior surfaces in the reaction chamber of a fluorescent instrument improve the sensitivity and detection limit of instruments making measurements in parts per billion (ppb) routinely possible.

The present invention broadly relates to a reaction cell including a reaction chamber having highly reflective interior surfaces where the surfaces are preferably highly polished and/or optically smooth. One preferred embodiment of the reaction cells of the present invention relates to a light reaction cell including a sample inlet, a sample outlet, an excitation light inlet port and a fluorescent detector outlet port. The cell also includes a reaction chamber having highly reflective, and preferably highly smooth, interior surfaces.

For the purpose of this invention, highly polished, optically smooth or optical smoothness is described in terms of the rms roughness or smoothness scale for measuring the smoothness or roughness of a surface. Generally, the rms roughness of the interior surfaces is less than about $200\mu"$ (microinches), preferably less than about $100\mu"$, particularly less than about $50\mu"$, especially less than about $30\mu"$, and most preferably less than about $10\mu"$. Alternatively, the rms roughness of the interior surfaces is between about $0.01\mu"$ (microinches) and about $200\mu"$, preferably between about $0.01\mu"$ and about $100\mu"$, particularly between about $0.05\mu"$ and about $50\mu"$, especially between about $0.1\mu"$ and about $30\mu"$ and most preferred between about $0.1\mu$ and about $10\mu"$.

For the purpose of this invention, highly reflective means that the surface should be generally capable of reflecting at least about 70% of the light striking the surface, preferably capable of reflecting at least about 80% of the light, particularly capable of reflecting at least about 90% of the light and especially capable of reflecting at least about 95% of the light and most preferably, capable of reflecting at least about 99% of the light. Generally, the reflectance properties will be preferably tuned to a given frequency range of light corresponding to the region of the electromagnetic spectrum that encompasses the fluorescent and/or excitation light of interest. For UV fluorescent spectroscopy, the desired range includes light generally in the wavelength range between about 100 nm and about 450 nm, preferred range between about 200 nm and about 300 nm and especially between about 200 nm and about 250 nm. For other fluorescent spectrometers, the frequency range or equivalently the wavelength range will encompass the desired excitation light range and/or the fluorescent light range of the fluorescing species.

The inventors have found that highly polished, highly reflective surfaces improve sensitivity and detection limit of fluorescent instruments. The inventors have also found that an orientation or direction of a pattern left in the material of the chamber during polishing affects the amount of improvement imparted to the chamber. Thus, if the chamber is generally cylindrically or rectangularly shaped with the excitation light traveling down the longitudinal (long) axis of the chamber (the length of the chamber), then the pattern of micro indentations, scratches, grooves, striations, streaks, or the like are preferably oriented substantially parallel to the longitudinal axis.

In one preferred design of the reaction cell of this invention, the interior surfaces are not only highly smooth and highly reflective, but are also contoured so that a portion of the fluorescent light emitted in a trajectory away from the detector port can be reflected and/or concentrated/focused through reflection at the contoured surfaces into and through a central region of the detector port. The contoured surfaces can also be designed so that a portion of the excitation light not absorbed by sample can be reflected and/or concentrated/focused into a central region of the reaction chamber. The contouring is preferably parabolic, but can be of any other contouring that focuses light such as a generally or substantially concaved surfaces. It should be recognized that the reaction cell can be constructed out of a single piece of material or can be constructed out of independent pieces of material and fitted together to make a complete cell. Of course, a cell made of several pieces must be fitted together to form a light tight chamber as is well known in the art.

Besides being smoothed by mechanical means such as polishing, the interior surfaces can be smoothed and rendered reflective by other well-known techniques that deposit smooth, reflective coating on surfaces, such as vapor deposition, ion or atom deposition, chemical deposition (e.g., solution plating), or electrochemical deposition (e.g., electroplating). Additionally, the smooth, reflective surfaces can be produced by removal processes such as ion or atom etching or any other similar techniques. Basically, any technique that can render a surface highly reflective and preferably optically smooth can be used to prepare the interior surfaces of the reaction cells of the present invention.

Although the interior surfaces of the chamber can be composed of any material capable of being rendered smooth and reflective to the desired excitation light and/or fluorescent light, the material should, preferably, also be chemically resistant to the chemical species present in the sample to be analyzed or to the photo-excited analogs thereof and break down products therefrom. Of course, chemical resistant is important only when the species in the sample react at or near the interior surface of the chamber causing the smoothness and/or reflective characteristics of the surface to deteriorate with the time of exposure. For example, if the sample includes sulfur species, the preferred interior surface materials are materials that do not readily reaction with the sulfur species such as, without limitation, stainless steel or other non-staining iron alloys, rhodium, osmium, ruthenium, platinum, or other highly reflective metals or alloys, mixtures or combinations thereof.

Another preferred embodiment of the reaction cell of the present invention includes a standard reaction cell having a sample inlet, a sample outlet, an excitation light port, a fluorescent light detector port and an insert generally conforming to the interior region of the cell and having an optically smooth, highly reflective interior surface(s). The insert can also include an alignment slot or member, a sample inlet aperture adapted to coincide with the cell sample inlet and a sample outlet aperture adapted to coincide with the cell sample outlet. The insert can further include apertures adapted to coincide with the excitation light port and the fluorescent detector port. The insert can be one piece or composed of multiple pieces that combine to form an insert that generally corresponds to the shape of the interior region of the reaction cell. Optionally, the cell can also include an excitation reflective end mirror for reflecting excitation light back into a central region of the insert.

For inserts composed of multiple parts or pieces, the insert should be constructed so that the seams where the pieces fit together do not significantly or substantially interfere with the fluorescent light reaching the detector port in the chamber as a result of reflection of the fluorescent light off the interior surface(s) of the insert. Thus, if the insert is cylindrically shaped and composed of two pieces that bisect the cylinder along is longitudinal (long) axis, then the seam is preferably oriented about 90° to the fluorescent light detector port in the reaction cell or chamber. Of course, if the seam is essentially optically smooth and does not significantly or substantially change the reflective properties of the interior surface, then the orientation of the seam is not critical.

Alternatively, the insert can be made of one material having either an interior or exterior highly reflective surface. If the insert has a mirrored exterior surface, then the interior surface of the insert is preferably smooth and the material making up the insert should be substantially transparent to the exciting light and/or the fluorescent light, such as, without limitation, glass, quartz, sapphire, diamond, ruby, or other similar substantially transparent materials. The material for use in insert of this type should transmits at least about 70% of the light, preferably at least about 80% of the light, particularly at least about 90% of the light and especially at least about 95% of the light and most preferably, at least 99% of the light. Of course, the transmittance characteristics of the material of choice will depend on the frequency range of the fluorescent light.

For inserts having smooth reflective interior surface coatings, the material out of which the insert is made can be of any material regardless of the materials transparency or chemical resistance. In fact, the insert does not have to be smooth provided that the coating imparts the desired smoothness and reflectivity to the insert.

For inserts including an excitation reflective mirror, the mirror preferably reflects at least about 70% of the excitation light, particularly at least about 80%, more particularly at least about 90% of the excitation light, especially at least about 95% of the excitation light, most particularly at least about 99% of the excitation light. The mirror can either be a separate member affixed to the distal end of the chamber opposite the excitation light port or affixed to or integral with the insert. The mirror can either have the reflective surface on its interior surface or on its exterior surface as described above for the insert.

General Details of the Apparatus

Referring now to FIGS. 1A–E, a first embodiment of a reaction cell of the present invention, generally 10 is shown, is generally rectangular and includes a body 12. The body 12 includes a sample inlet 14 located near a first longitudinal end 16 and a sample outlet 18 located near a second longitudinal end 20. The first longitudinal end 16 has an excitation light port 22 associated therewith. The port 22 is the aperture through which the light generated by a light source enters the chamber and results in excitation of a portion of the molecules in the sample within the chamber.

The body 12 further includes a fluorescent detector port 24 oriented substantially orthogonal (at or near a 90° angle) to the source port 22. The body 12 also includes a reaction chamber 26 having an interior surface 28. In this embodiment, the chamber 26 is essentially cylindrical. The surface 28 is smooth and reflective, preferably optically smooth and highly reflective to the fluorescent light produced by the excited species in the chamber 26.

The cell 10 can further include grooves or indentations 30 associated with the ports to accommodate O-rings used to seal the cell 10 in a light tight fashion. The cell 10 can also include other ports 32 having grooves 30 associated therewith that are generally sealed by cover plates (not shown). Of course, the cell 10 can also be constructed so that there is no opening at the end 20.

Figure 1F:
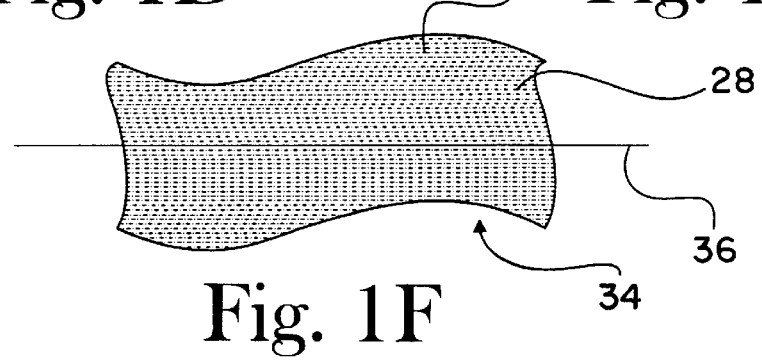
Figure 2A:
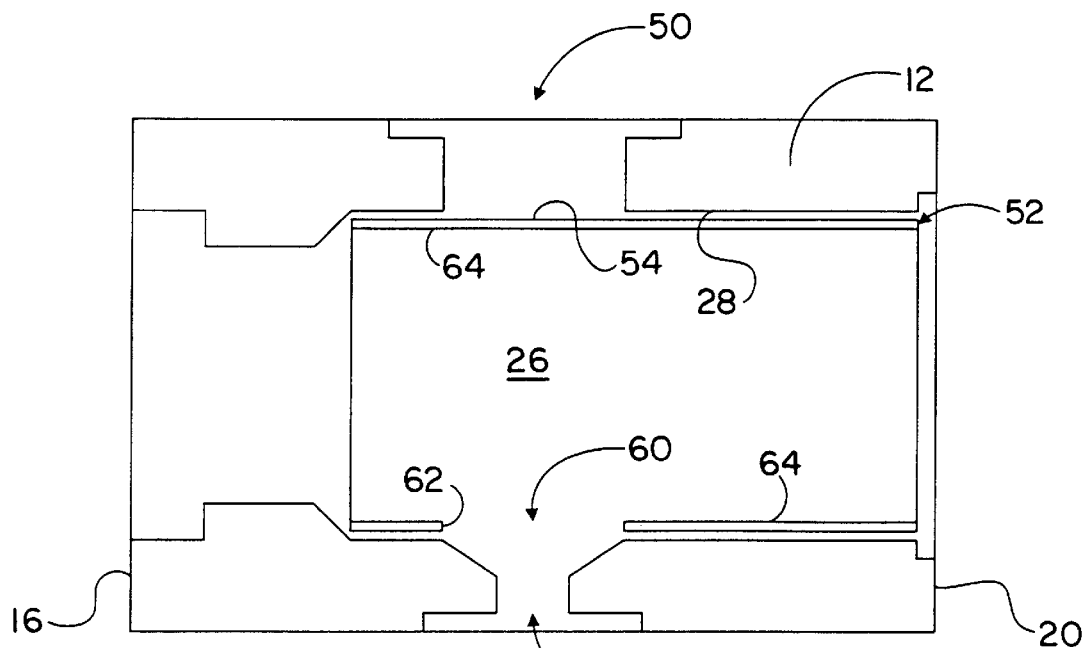
FIG. 2A is a cross-sectional top view of second embodiment of a reaction cell of the present invention including an insert.
Figure 2B:
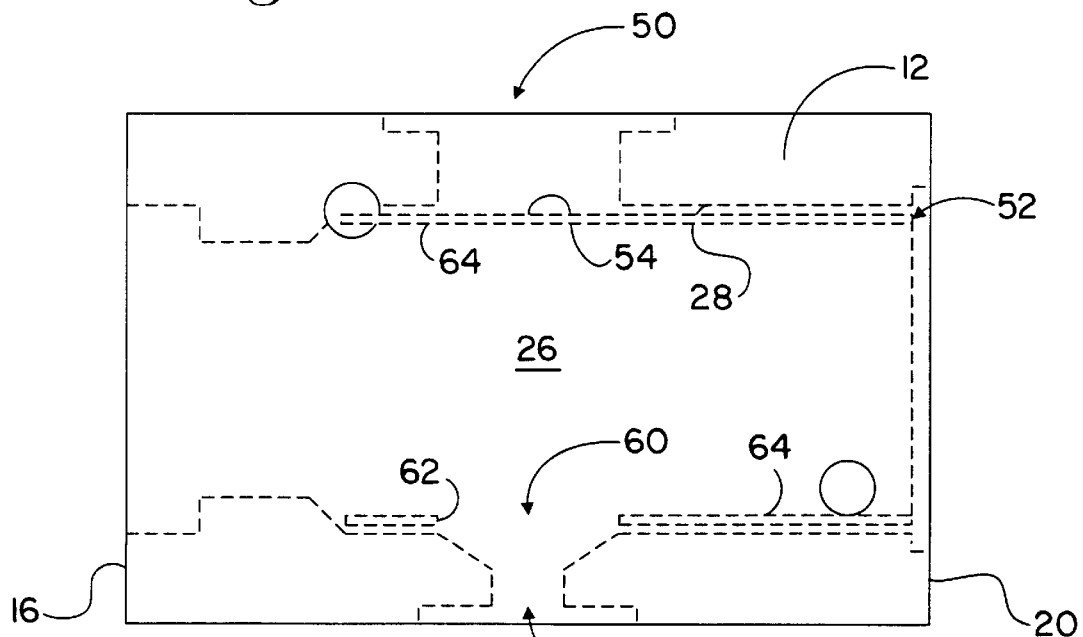

A portion 34 of surface 28 is shown magnified in FIG. 1F which is oriented in reference to a longitudinal axis 36 of the reaction cell 10. If the surface is rendered optically smooth and highly reflective by polishing, the polishing is preferably performed in such a way that micro scratches 38 in the surface 28 are preferentially oriented substantially parallel to a longitudinal axis 36 of the reaction chamber 26. The inventors have found that radially oriented scratches do not increase the sensitive and lower the detection limit of the reaction cell 10 as much as when the scratches are oriented substantially parallel to the longitudinal axis 36 of the cell 10. Of course, any increase in the smoothness and reflectivity indices of the surface 28 will result in an increase in sensitivity and a reduction in detection limit of fluorescent instruments, including UV fluorescent instruments. Of course, this same preference for the orientation of polishing scratches is equally true for any other embodiment herein disclosed where the interior surface of the device is polished such as interior surface 64 of insert 52 of FIGS. 2A–F and interior surface 102 of FIG. 6.

Referring now to FIGS. 2A–E, another embodiment of the reaction cell of the present invention, generally 50 is shown, which includes all the components of the cell 10 as well as a reaction chamber insert 52 conforming to the reaction chamber 26. Additionally, because this embodiment includes an insert, the reaction cell can also include an unused port opposite the detector port 24. Many standard reaction cells have ports associated with four sides of the cells. In the cell of FIGS. 1A–E, a port opposite the detector port 24 would not work as effectively because the edges associated with the port would tend to scatter both fluorescent light and excitation light.

Figure 3A:
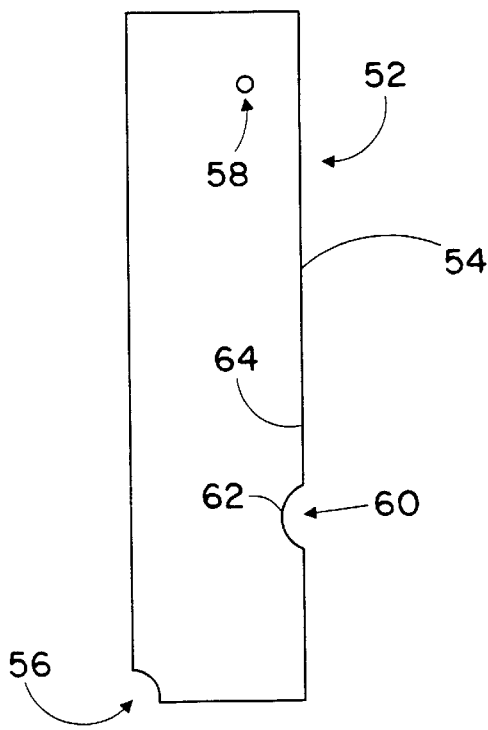
FIG. 3A is a first side view of one embodiment of a reaction cell insert of the present invention.
Figure 3B:
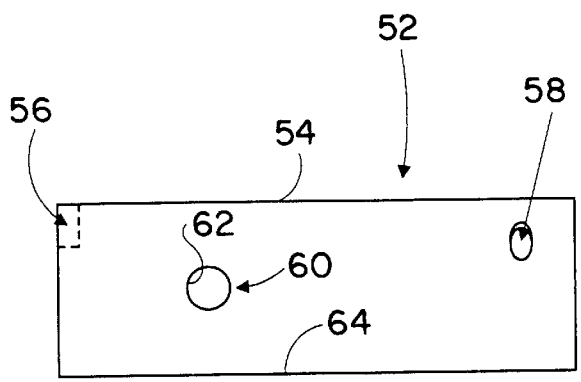
Figure 3C:
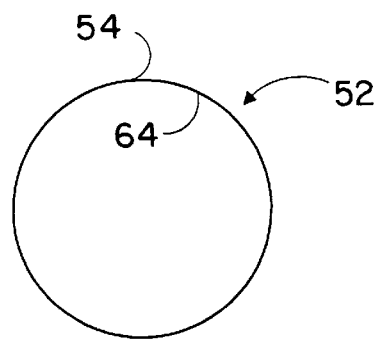

FIGS. 3A–C show a first embodiment of the insert 52, which includes an exterior surface 54 adapted to be inserted into the chamber 26 and is preferably in contact or in near contact with the interior surface 28 of the chamber 26 (the insert is designed to fit snugly in the chamber 26), an inlet notch 56 adapted to engage the sample inlet port 14, an outlet aperture 58 which is coincident with the sample outlet port 18, and a detector port aperture 60 which coincides with the detector port 24.

Preferably, the aperture 60 is larger than the port 24 in diameter so that light scattering at a edge 62 of the aperture 60 does not interfere with the detection of light in a fluorescent light detector. If the aperture 60 is substantially the same diameter or of a diameter less then the diameter as the port 24, then the edge 62 is preferably painted with a non-reflective, absorbing paint to reduce light scattering at the edge 62. The insert 52 also includes an interior surface 64 that is preferably optically smooth and highly reflective. Instead of the inlet notch 56, the insert 52 can include a sample inlet aperture (not shown) that coincides with the cell sample inlet 14 and a separate alignment notch (not shown) that allows the insert 52 to be inserted into the chamber 26 and aligned so that the apertures of the insert 52 coincide with the apertures 14, 18 and 24 of the cell 50. Additionally, the aperture 60 and the port 24 can be threaded on their internal diameter and coated with a non-reflective coating to reduce the amount of stray light reflected off their internal diameter.

Referring now to FIGS. 3D–E, a second embodiment of the insert 52 is shown to include an oval-shaped aperture 61 instead of a circular aperture as in FIGS. 3A–B. Although the oval-shaped aperture is shown with cusps, the aperture can also be a smooth oval shape as well. Referring now to FIGS. 3F–G, a third embodiment of the insert 52 is shown to include a plurality of slit-like apertures 63 in place of a single aperture. Although three embodiments of inserts having different types of apertures coinciding to the detector port 24, it should be recognized that the aperture(s) coinciding with the detector port 24 can be of any shape or number provided that the aperture(s) do not substantially interfere with the amount of light passing through the detector port 24 and into a detector.

Referring now to FIG. 4A–C, a fourth embodiment of a reaction chamber insert of the present invention, generally 70 is shown, which includes a first longitudinal section 72 and a second longitudinal section 74. The two sections 72 and 74 assemble to form the insert 70 having seams 76. The assembled insert 70 also includes a combined exterior surface 78 adapted to be in contact or in near contact with an interior surface 28 of the chamber 26, a notch 56 which coincides with the sample inlet port 14, an aperture 58 which is coincident with the sample outlet port 18, and a reactor aperture 60 which coincides with the detector port 24. Again preferably, the aperture 60 is larger than the port 24 in diameter so that light scattering at an edge 62 of the aperture 60 does interfere with the detection of light in a fluorescent light detector. The insert 70 also includes a combined interior surface 80 that is optical smooth and high reflective.

Figures 5A, 5B:
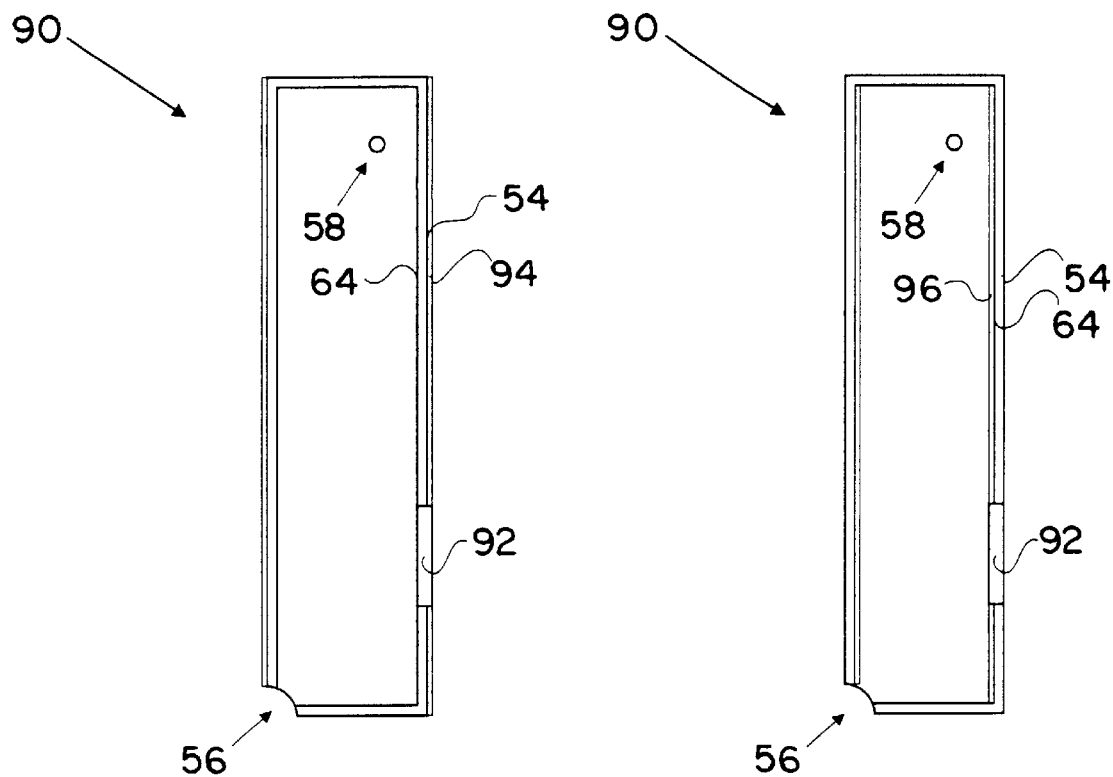
Figure 5C:
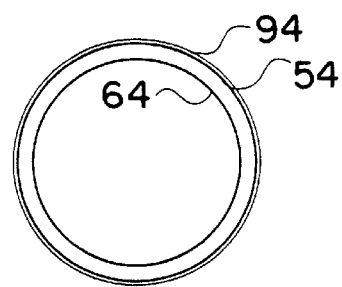

Referring now to FIGS. 5A–C, yet another embodiment of a reaction chamber insert, generally 90 is shown, which includes an exterior surface 54 adapted to be in contact or in near contact with an interior surface 28 of the chamber 26, a notch 56 adapted to engage the sample inlet port 14 and an aperture 58 which is coincident with the sample outlet port 18, and a window 92 which coincides with the detector port 24. Optionally, the window 92 can be replaced with the aperture 60 as described above coinciding with the detector port 24.

The insert 90 also includes an interior surface 64. In a first sub-embodiment, the interior surface 64 is smooth, while the exterior surface 54 is coated with a reflective coating 94 as shown in FIGS. 5a and c. In this sub-embodiment, the insert 90 is constructed of a material like quartz or glass that is substantially transparent to the fluorescent light. The window 92 is also made of such substantially transparent material.

In a second sub-embodiment, the insert 90 has a smooth and reflective coating 96 associated with the interior surface 64 as shown in FIG. 5b. In this sub-embodiment, the insert 90 can be made out of any material because the reflective coating is on the interior surface 64 of the insert 90.

Again, the interior surface 92 is preferably optically smooth, while the reflective coatings 94 or 96 are preferably highly reflective. The reflective coating should be sufficient thick to reflect about at least 70% of the light in the frequency range of interest, preferably about at least 80% of the light, particularly about at least 90% of the light, and especially about at least 99% of the light.

Figure 6:
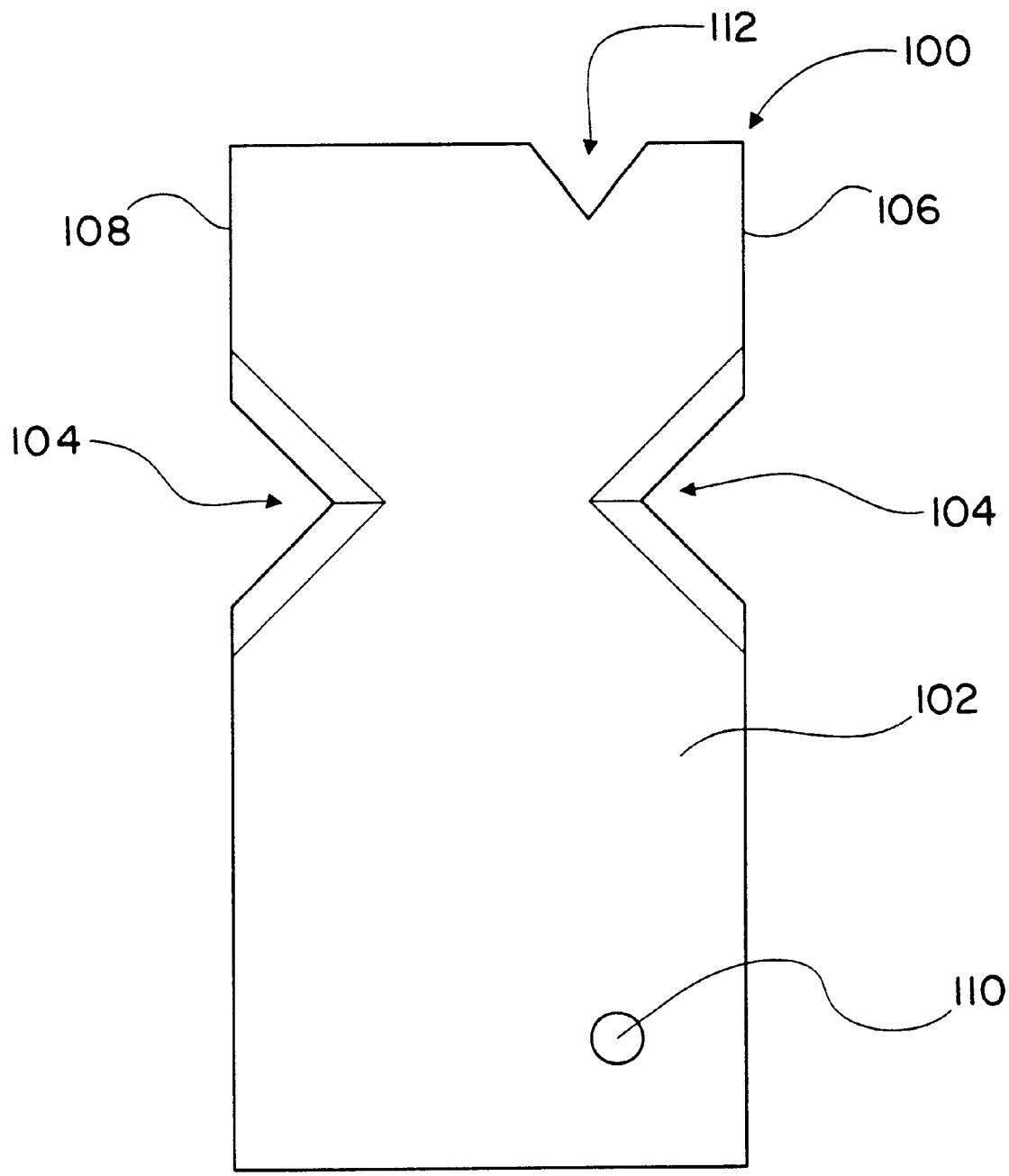
FIG. 6 is a plan view of another embodiment of a reaction cell insert of the present invention.

Referring now to FIG. 6, still another insert of the present invention, generally 100 is shown, which includes a thin sheet 102 having notches 104 associated with a first edge 106 and a second edge 108 where the notches 104 are designed to combine to form an aperture when the sheet 102 is bent (rolled up) to conform to the chamber 26 of the cell 10. The sheet 102 also includes an aperture 110 adapted to coincide with the sample outlet 18 and an alignment notch 112 adapted to engage the sample inlet 14 which generally protrudes into the chamber 26.

Figure 7A:
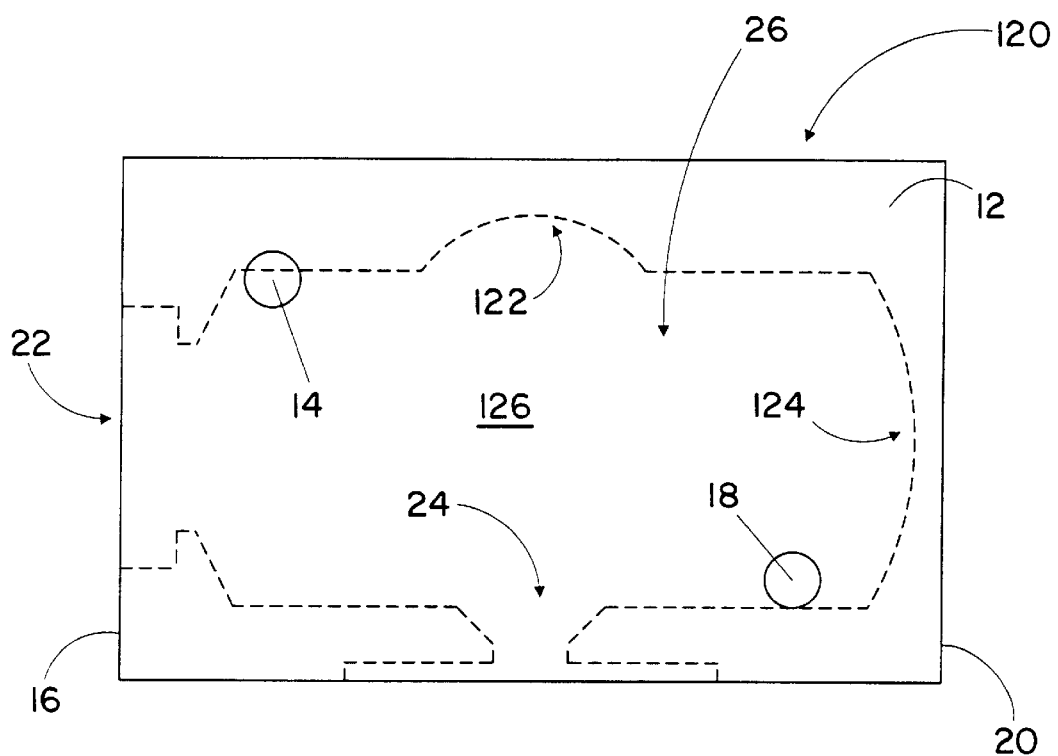
FIG. 7A is a top cross-sectional view of a first embodiment of a cell of the present invention having contoured reflective surfaces for focusing reflected excitation light into the central region of then and fluorescent light into the detector port.

Referring now to FIG. 7A, another reaction cell of the present invention, generally 120 is shown to include a body 12, a sample inlet 14 located near a first end 16, a sample outlet 18 located near a second end 20, an excitation light entry port 22, and a fluorescent light detector port 24 preferably oriented substantially orthogonal to the entry port 22. The cell 120 further includes a light/sample reaction chamber 26 having a first contoured interior surface 122 adapted to focus a portion of the fluorescent light emitted by the fluorescing species into the detector port 24 through reflection. The contoured surface 122 is smooth and reflective and preferably optically smooth and highly reflective to the frequency range of the fluorescing species of interest. The contoured surface 122 is generally concaved, preferably circularly concaved or elliptically concave and particularly parabolically concaved. The chamber 26 also has a second contoured interior surface 124 adapted to focus a portion of excitation light into a center 126 of the chamber through reflect. As with the first surface 122, the second surface 124 should preferably be optically smooth and highly reflective and constructed of a material highly reflective to the frequency range of the excitation light.

Although cell 120 is a unitary cell design like the cell, the contoured surface 122 can also be incorporated into an insert. Moreover, an insert can be designed to incorporate the surface 124 by closing the insert at the end opposite the excitation port opening of the insert.

Figure 7B:
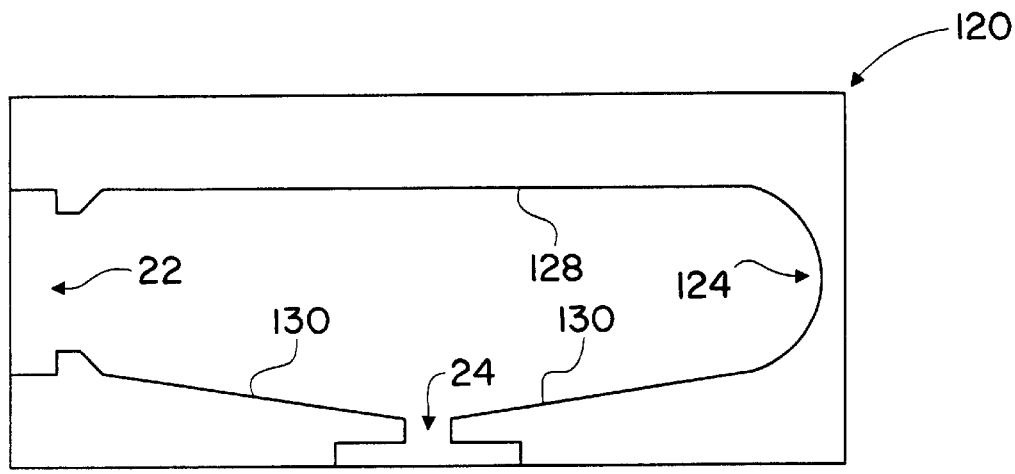
FIG. 7B is a top cross-sectional view of a second embodiment of a cell of the present invention having contoured reflective surfaces for focusing reflected excitation light into the center region of the cell and fluorescent light into the detector port.
Figure 7C:
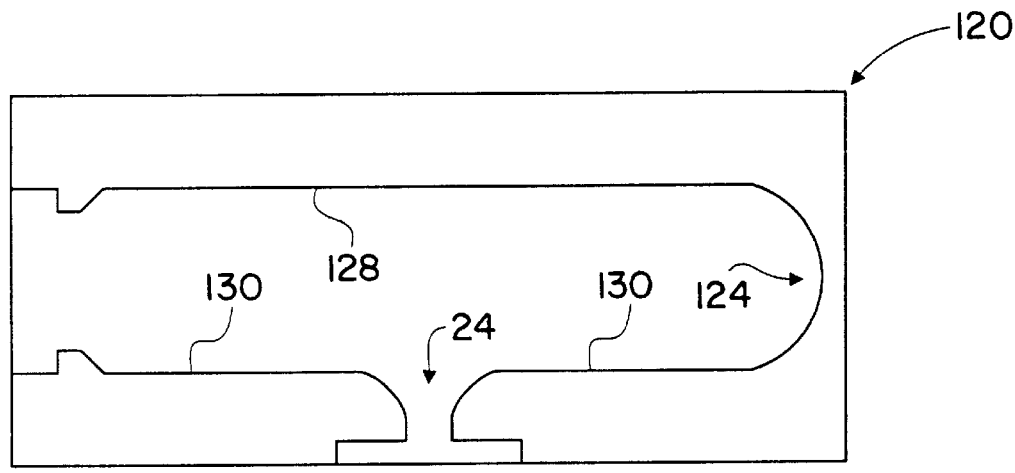
FIG. 7C is a top cross-sectional view of a third embodiment of a cell of the present invention having contoured reflective surfaces for focusing reflected excitation light into the center region of the cell and fluorescent light into the detector port.
Figures 7D, 7E:
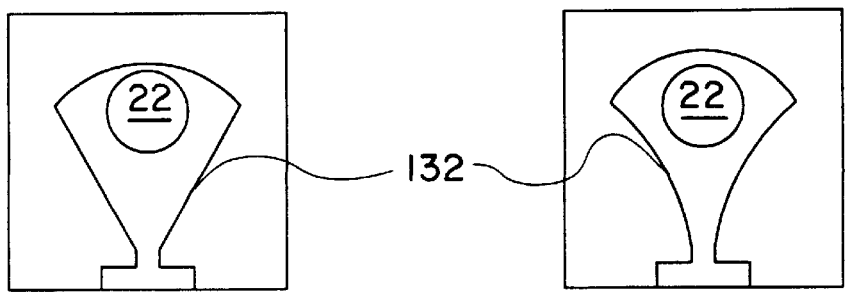
FIG. 7D is a first side cross-sectional view of the cells of FIGS. 7B & C.
FIG. 7E is a second side cross-sectional view of the cells of FIGS. 7B & C.

Referring to FIGS. 7B–E, two additional embodiments of a contoured reaction cell 120. In FIGS. 7B, D, and E, the cell 120 includes the excitation light focusing surface 124, a fluorescent focusing surface 128, gently angled detector port surfaces 130 and straight or convex longitudinal surfaces 132. In FIGS. 7C, D and E, the cell 120 is essentially the same of the cell in FIG. 7B, except the cell 120 of FIG. 7C has straight detector port surfaces 130. It should be recognized that the chamber of the cells of FIGS. 7B–E have a generally key-hole shape when viewed in cross-section as shown in FIGS. 7D and E. Additionally, the insert of the present invention can be made to have the same cross-section as the chambers of the cell of FIGS. 7E and F. Although the cell of FIG. 7A will improve sensitivity and detection limit of a reaction cell so designed, the cells of FIGS. 7B and C are preferred designed because these cells are designed to substantially eliminate any scattering of excitation light entering the reaction chamber of the reaction cell. Of course, the cell of FIGS. 7D and E also include sample inlet and outlet ports as in all other embodiments of the cells of the present invention.

Figure 8:
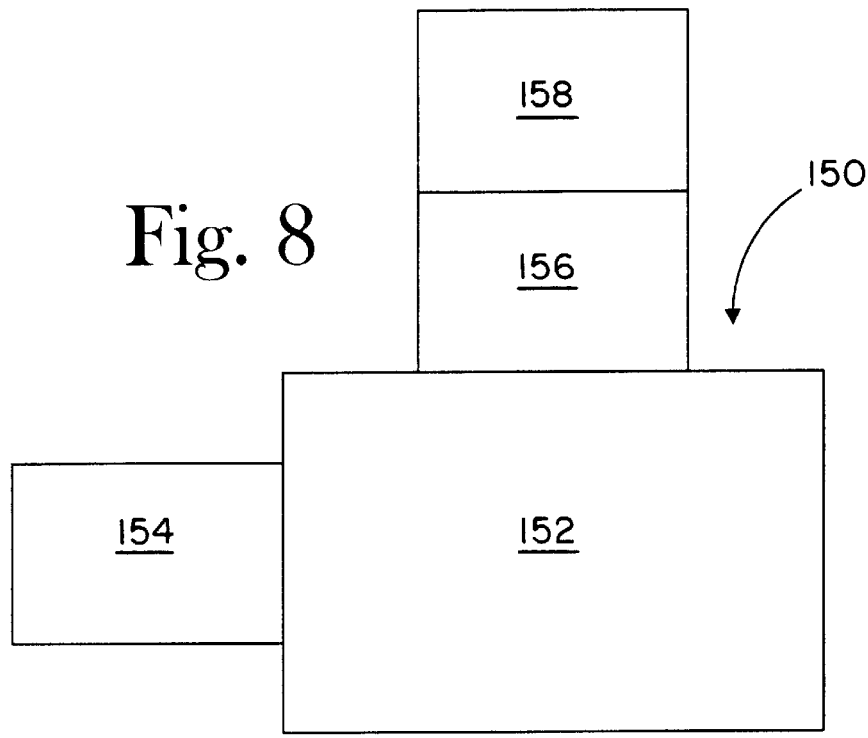
FIG. 8 is a block diagram of a fluorescent detection system incorporating a reaction cell of the present invention.

Referring now to FIG. 8, a fluorescent detection assembly generally 150 is shown, which includes a light reaction cell 152, a light source component 154 associated with the cell 152, a fluorescent detector component 156 associated with the cell 152, and a fluorescent analyzing component 158 associated with the detector component 156. The reaction cell 152 can be any of the reaction cells described above.

Figure 9:
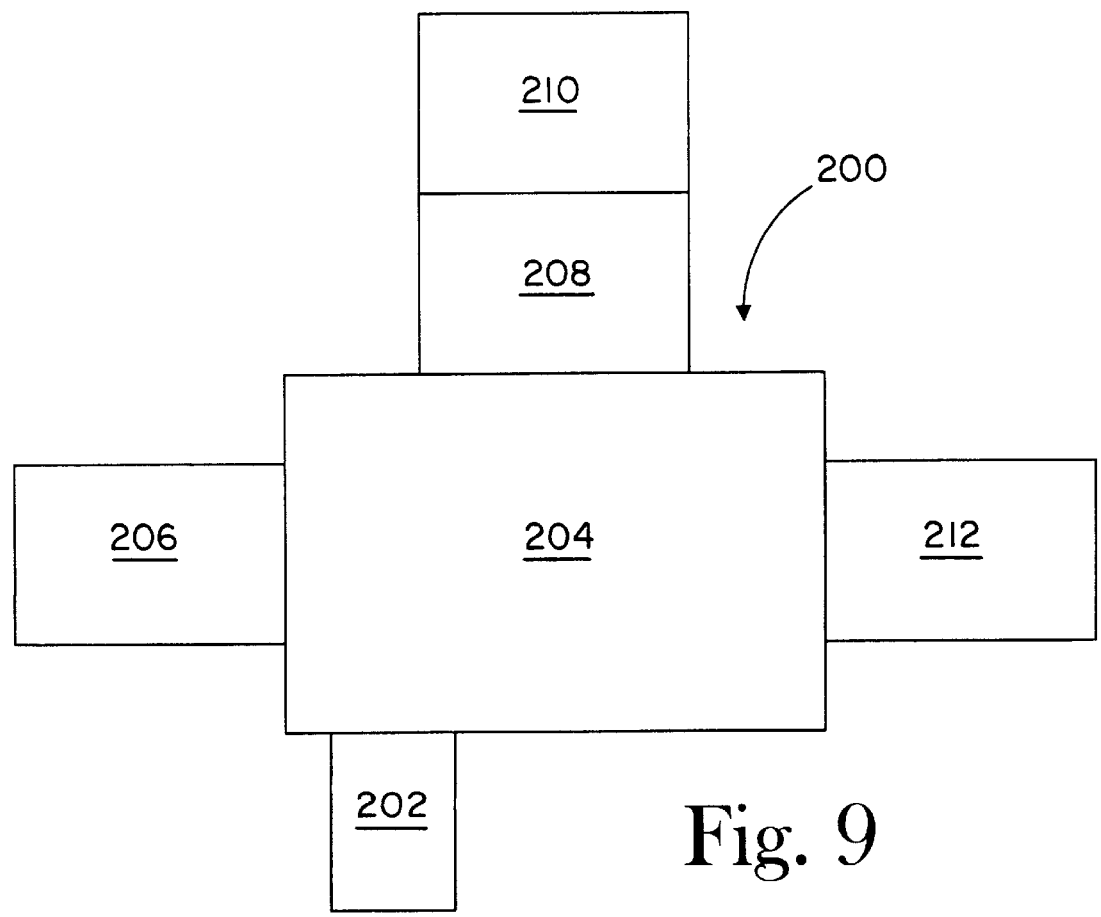
FIG. 9 is a block diagram of a fluorescent instrument incorporating a reaction cell of the present invention.

Referring now to FIG. 9, a fluorescent instrument generally 200, which includes a sample supply component 202, a light reaction cell 204, a light source component 206 associated with the cell 204, a fluorescent detector component 208 associated with the cell 204, a fluorescent analyzing component 210 associated with the detector 208 and a sample outlet component 212. The reaction cell 204 can be any of the reaction cells described above.

The light source components 206 generally includes a light source, a collimator and filters. The light source generates light in a given frequency range (e.g., the UV range); the collimator concentrates the light so that a majority of the light energy can be focused into the reaction cell and concentrated into the center of the reaction chamber; and the optical filters are used to restrict the frequency range of the excitation light.

The detector component 208 is generally a photomultiplier tube, although other light detection and amplifying devices can be used as well as is well-known in the art. The component 208 also generally includes lens and filters designed to direct the fluorescent light into the detector. The analyzing component 210 associated with the detector component 208 can be any device in electrical communication with the detector and capable of receiving and converting an output signal of the detector into a user readable format or a recordable format.

The sample supply component 202 can include any analytical separation instrument such as, without limitation, a GC, LC, HPLC, MPLC or a similar sample separation unit. The component 202 can further include a sample transformation units such as, without limitation, an oxidation device, a reductive device, an oxidative device coupled with a reductive device or any other unit that chemically transforms sample components into components that actively fluoresce when excited with a given wavelength range of light such as UV light. For sulfur and nitrogen analysis after HPLC separation, the component 202 would be an HPLC coupled with an oxidative furnace which would convert nitrogen and/or sulfur components in the sample to nitrogen and sulfur oxides.

Although the present invention has been primarily centered around fluorescent spectroscopy, the reaction cells of this invention should find equal utility in phosphorescent spectroscopy of in any other spectroscopy involving light excitation and/or light emission.

EXAMPLES

The following examples illustrate the usefulness of the reaction cells of the present invention in improving the sensitivity and reducing the detection limit (making smaller amount of sample detectable) of UV fluorescent instruments. In the examples, the UV fluorescent instrument is adapted to detect and analyze the amount of sulfur or nitrogen in a sample. Although these examples are designed to detect the fluorescence of sulfur or nitrogen species, the reaction cells of the present invention fmd utility in any UV fluorescent instrument.

The examples are all directed to the detection of sulfur dioxide which is formed by burning a sample containing 250 ppb sulfur as $H_2S$ in argon. About 700 cc/min of sample is feed to a 1000° C. pyrotube in the presence of about 80 cc/min oxygen, where the oxygen is sufficient to convert all or substantially all of the $H_2S$ to sulfur dioxide for later analysis. The oxidized sample was then forwarded to a detector cell equipped with a PMT tube, a PMT H/V tube 575. VDC. All tests used the same PMT tube bias voltage. The excitation source was the same for all experiments and the detector was also the same for all experiments. The data from each experiment shows the baseline response (pure argon) to the sample response. Generally, two successive sample amount were run in each experiment. The emitted light consisted of the fluorescent spectrum of electronically excited sulfur dioxide. For all tests the chart recorder was set to 200 mV (millivolts) full scale. When the signal was amplified 50 times full scale, the chart effectively became a 4 mV full scale plot (half of a major division represented 0.2 mV during x50 portions of each example).

Example 1

This example illustrates the baseline, response and noise of a first fluorescent detector cell to 250 ppb sulfur in argon where the standard detector cell is black and roughly textured.

Figure 10:
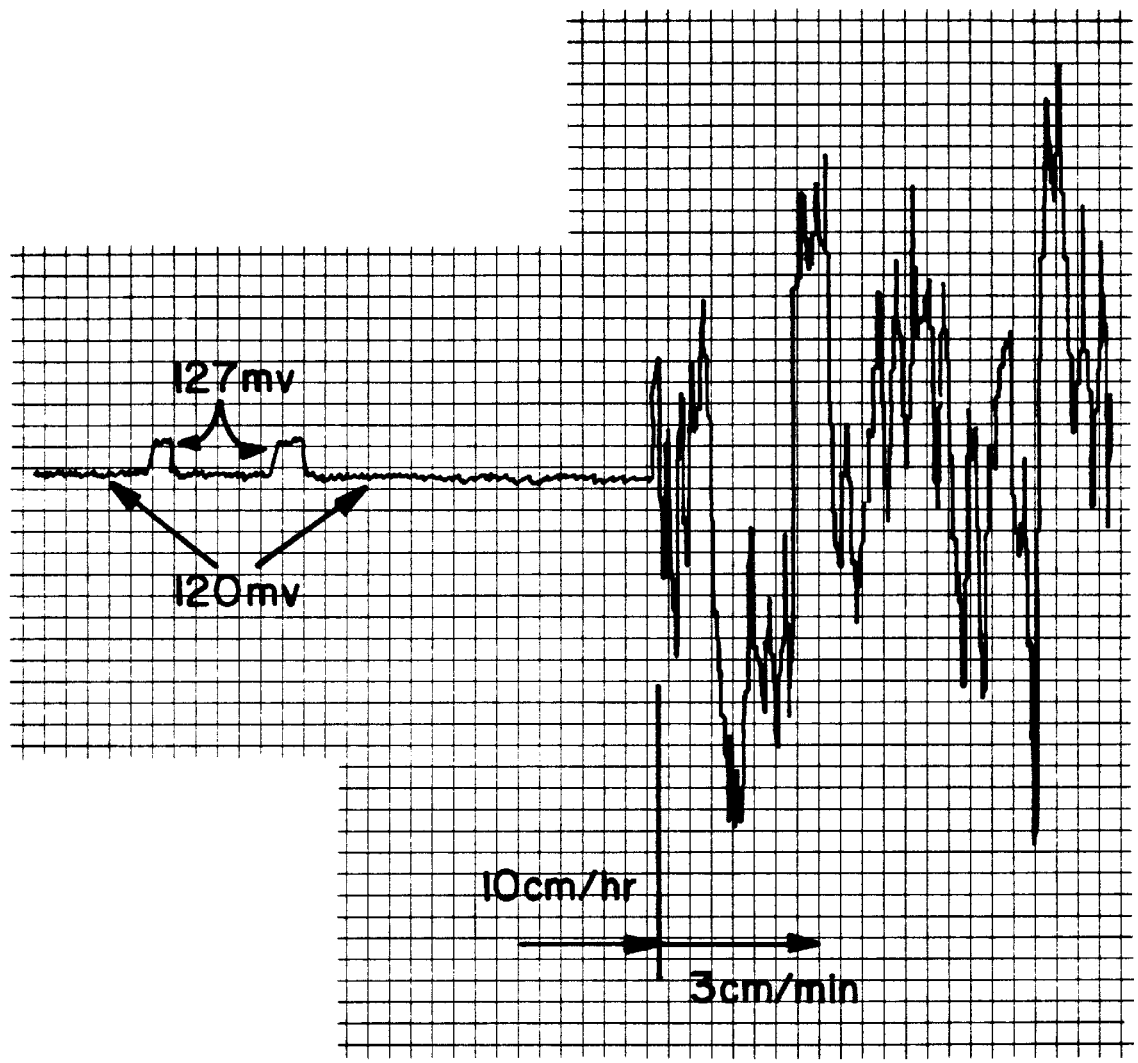
FIG. 10 is a graphical depiction of data from a first cell with no insert.

The baseline was established using pure argon at 120 mV. Two samples containing 250 ppb $H_2S$ in argon were successively introduced into the oxidation furnace and the resulting $SO_2$ produced to two about 7 mV response peaks as shown in FIG. 10, with the chart recorder run at 10 cm/hr. The chart recorder was then expanded 50 times, zeroed, filtered with a 2 second RC filter and run at 3 cm/min to obtain a visual measure of baseline noise. The baseline for the standard cell can be seen to be considerably noisy.

Examples 2

This example illustrates the baseline, response and noise of the first fluorescent detector cell to 250 ppb $H_2S$ in argon where the detector cell includes a circularly polished insert having easily visible grains in the circumferential direction.

Figure 11:
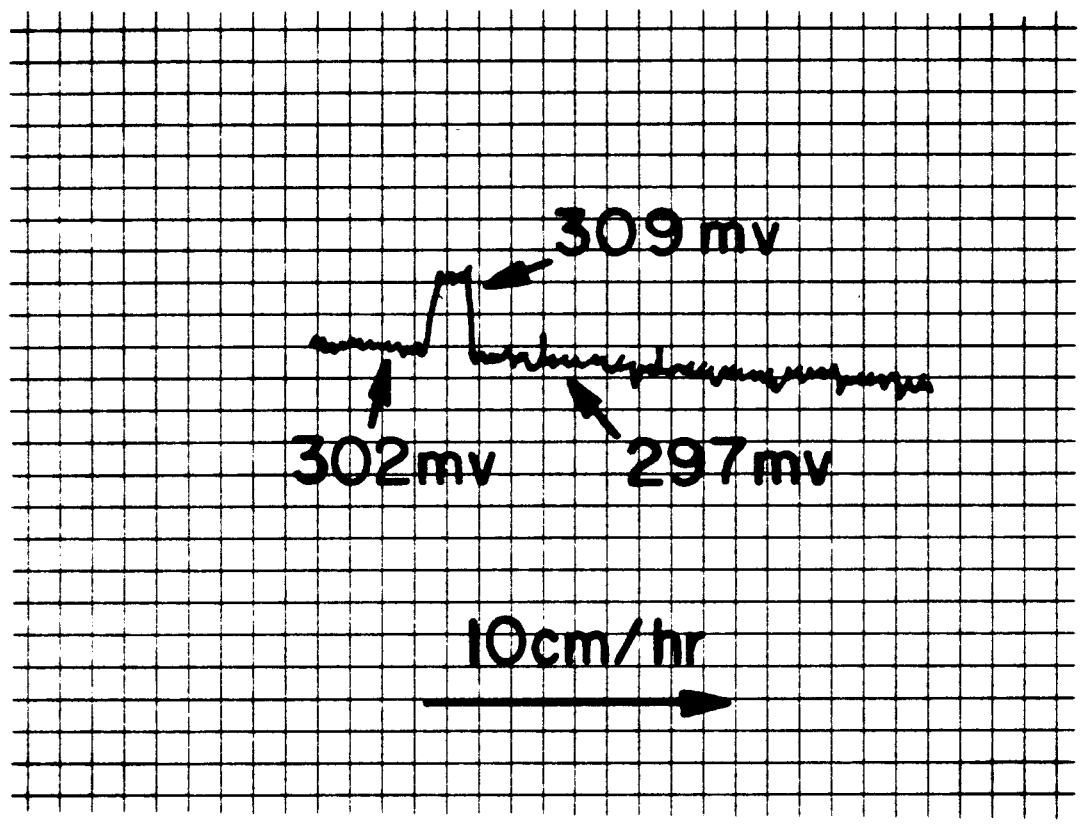
FIG. 11 is a graphical depiction of data from the first cell with an insert having an interior surface with easily visible radial scratches.

The baseline was established for pure argon at 302 mV, but drifted down during this run. The chart recorder was zero offset negative to get signal on chart. One sample containing 250 ppb $H_2S$ in argon was introduced into the oxidation furnace and the resulting $SO_2$ produced about a 9 mV response peak (309–300) as shown in FIG. 11, with the chart run at 10 cm/hr. Because the baseline response was difficult to keep on the chart, no expanded scale data was taken. But, the thickness of the baseline is evidence of considerable noise in the baseline signal and the response signal. In fact, the thickness of the baseline relative to the height of the signal is a crude measure of signal to noise.

Examples 3

This example illustrates the baseline, response and noise of the first fluorescent detector cell to 250 ppb $H_2S$ in argon where the detector cell includes a cylindrical insert having a polished interior surface with barely visible scratches oriented along the length of the insert.

Figure 12:
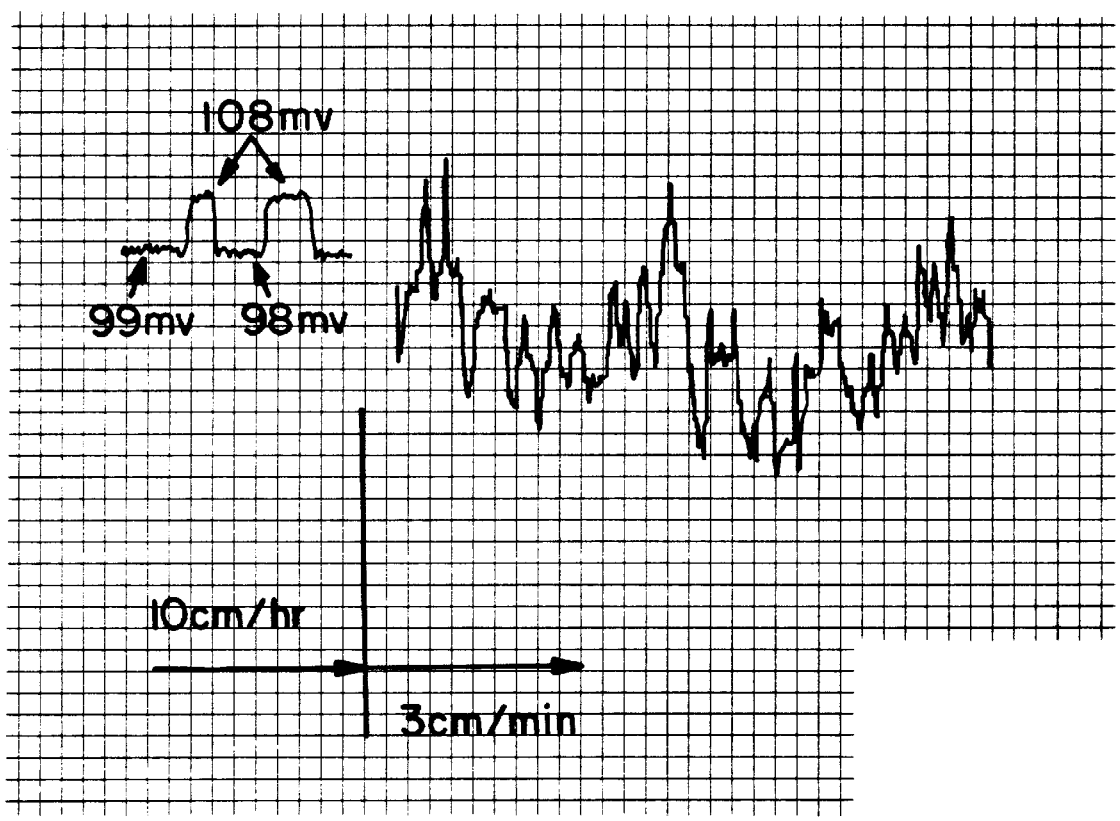
FIG. 12 is a graphical depiction of data from the first cell with an insert having a polished interior surface with barely visible lengthwise scratches.

The baseline was established with pure argon at 99 mV with a slight downward drift. Two samples containing 250 ppb $H_2S$ in argon were introduced into the oxidation furnace and the resulting $SO_2$ produced two response peaks of about 10 mV (108–98) as shown in FIG. 12, with the chart recorder run at 10 cm/hr. The chart recorder was then expanded 50 times, zeroed, centered, filtered with a 2 second RC filter and run at 3 cm/min to obtain a visual measure of baseline noise. The baseline of the normal recording and the expanded scale shows considerable less noise and a greater sensitivity than the results of example 1 or 2.

Examples 4

This example illustrates the baseline, response and noise of the first fluorescent detector cell to 250 ppb $H_2S$ in argon where the detector cell includes a cylindrical insert having a clean, sand blasted interior surface.

Figure 13:
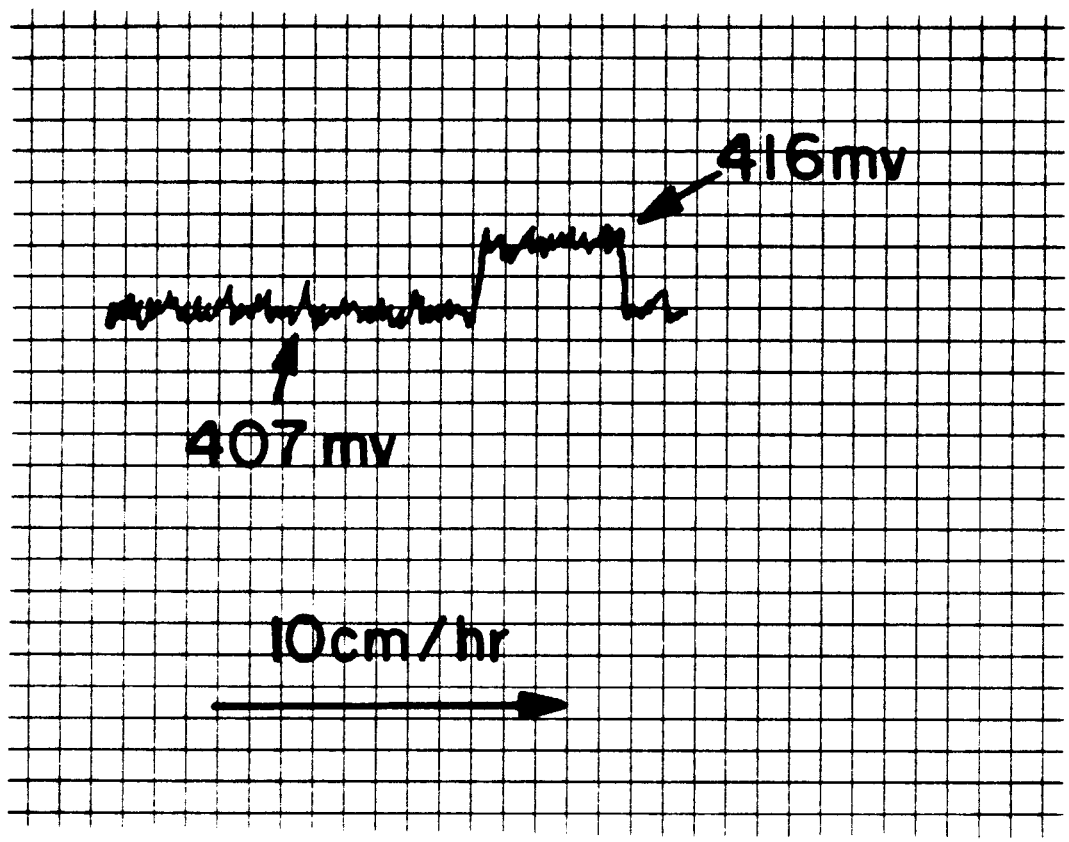
FIG. 13 is a graphical depiction of data from the first cell with an insert having sandblasted interior surface.

The baseline was established using pure argon at 407 mV. One sample containing 250 ppb $H_2S$ in argon was introduced into the oxidation furnace and the resulting $SO_2$ produced a response peak of about 9 mV as shown in FIG. 13. The chart recorder zero offset was negative to get the signal on the chart, with the chart recorder run at 10 cm/hr. The baseline signal and response signal are thick which is a crude and relative measure of signal to noise. Compared to example 3, this highly rough insert gave very poor results similar to the insert of example 2.

Examples 5

This example illustrates the baseline, response and noise of the first fluorescent detector cell to 250 ppb $H_2S$ in argon where the detector cell includes a cylindrical brass, rhodium plated interior surface that was highly polished prior to plating. The interior surface was highly reflective and smooth.

Figure 14:
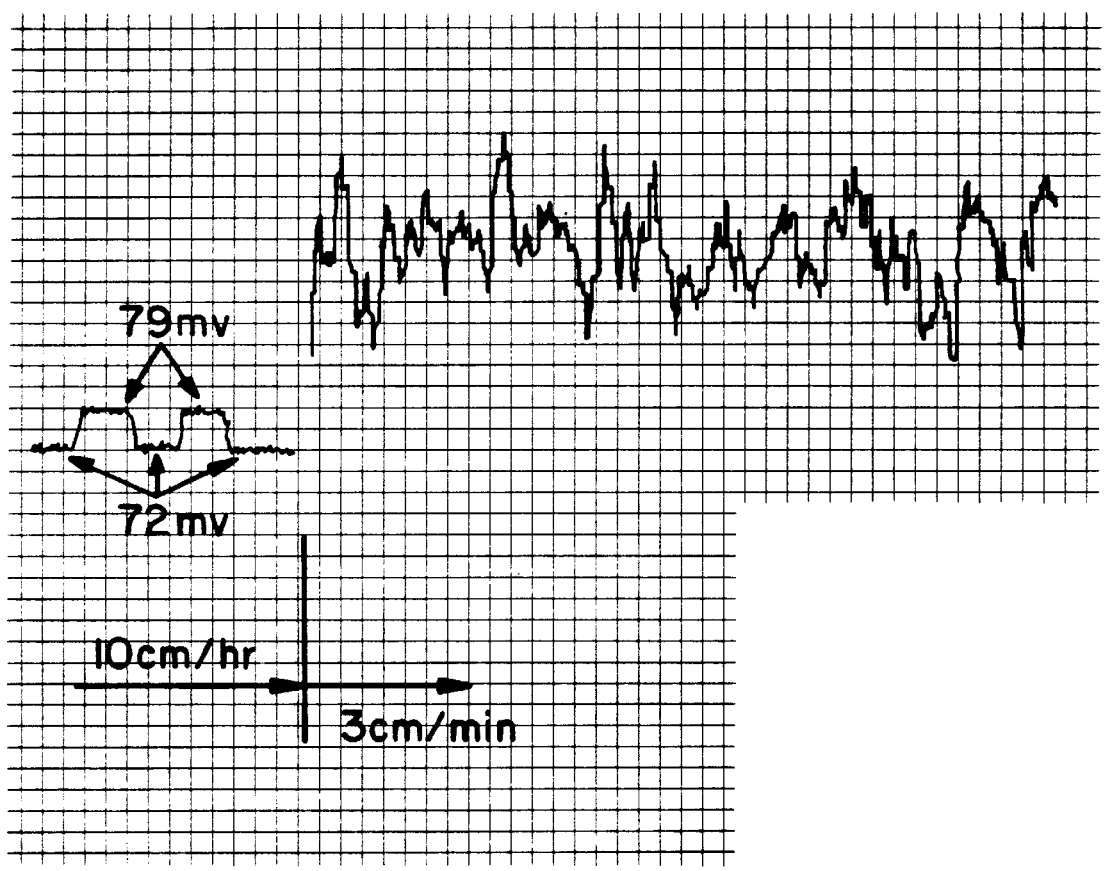
FIG. 14 is a graphical depiction of data from the first cell with a brass insert having a rhodium plated interior surface that was polished before plating.

The baseline was established using pure argon at 72 mV. Two samples containing 250 ppb $H_2S$ in argon were introduced into the oxidation furnace and the resulting $SO_2$ produced two response peaks of about 7 mV as shown in FIG. 14, with the chart recorder run at 10 cm/hr. The chart recorder was then expanded 50 times, zeroed, centered, filtered with a 2 second RC filter and run at 3 cm/min to obtain a visual measure of baseline noise. The baselines of the normal scale and expanded scale recordings show considerably less noise than the results of example 1, 2 and 4, and similar to the response in example 3; while the sensitivity was similar to example 1.

Examples 6

This example illustrates the baseline, response and noise of the first fluorescent detector cell to 250 ppb $H_2S$ in argon where the detector cell includes a cylindrical insert having a interior surface that was highly polished with barely visible circumferential or radial scratches.

Figure 15:
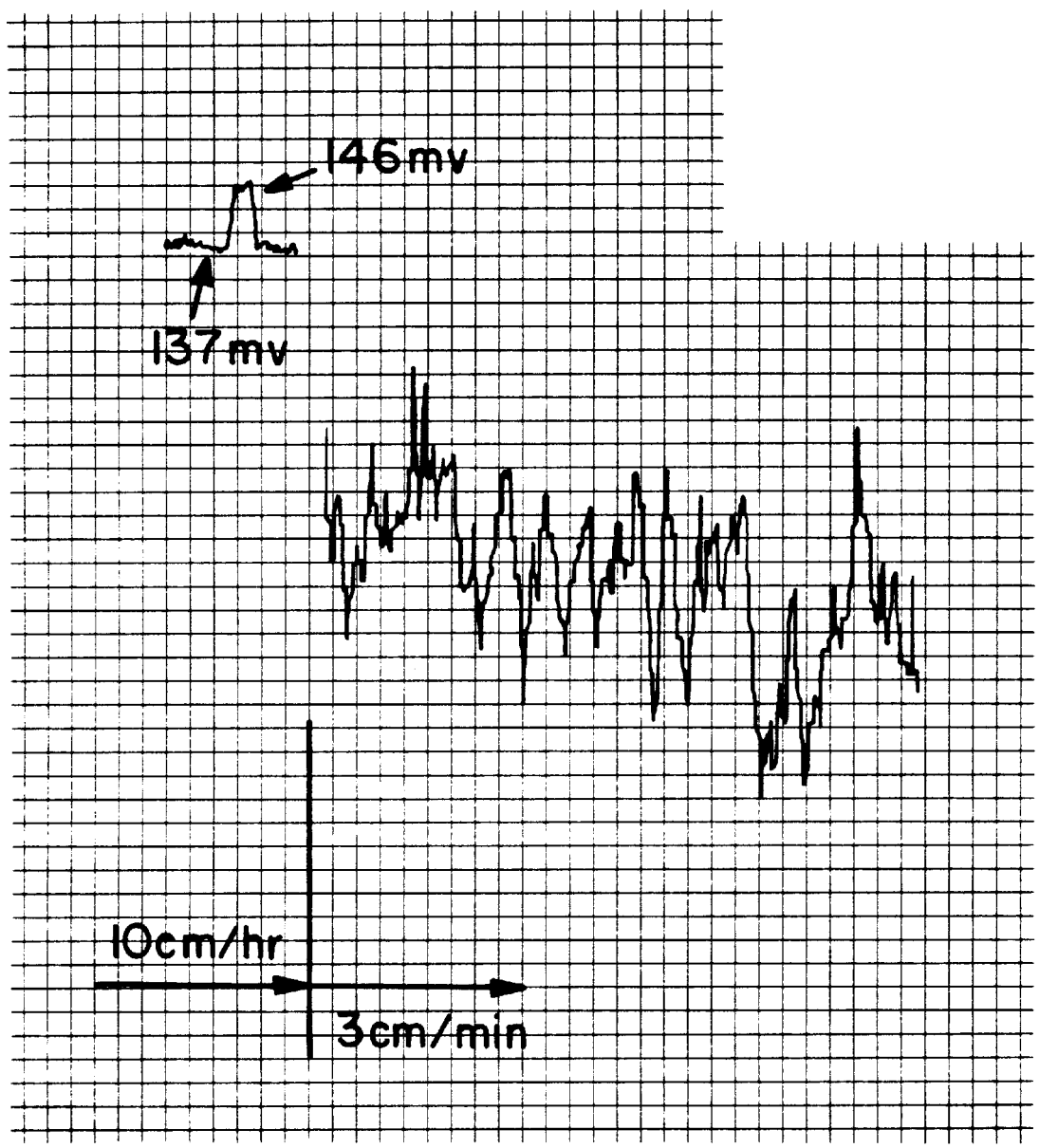
FIG. 15 is a graphical depiction of data from the first cell with an insert having a polished interior surface with barely visible radial scratches.

The baseline was established using pure argon at 137 mV with a slight downward drift during this run. One sample containing 250 ppb $H_2S$ in argon was introduced into the oxidation furnace and the resulting $SO_2$ produced about a 9 mV response peak as shown in FIG. 15, with the chart recorder run at 10 cm/hr its normal settings. The chart recorder was then expanded 50 times, zeroed, centered, filtered with a 2 second RC filter and run at 3 cm/min to obtain a visual measure of baseline noise. The baselines of the normal scale and the expanded scale recordings show considerably less noise and a greater sensitivity than the results of example 1, 2 and 4, and similar to the responses in example 3 and 5.

Examples 7

This example illustrates a retest of cell of example 1 without an insert.

Figure 16:
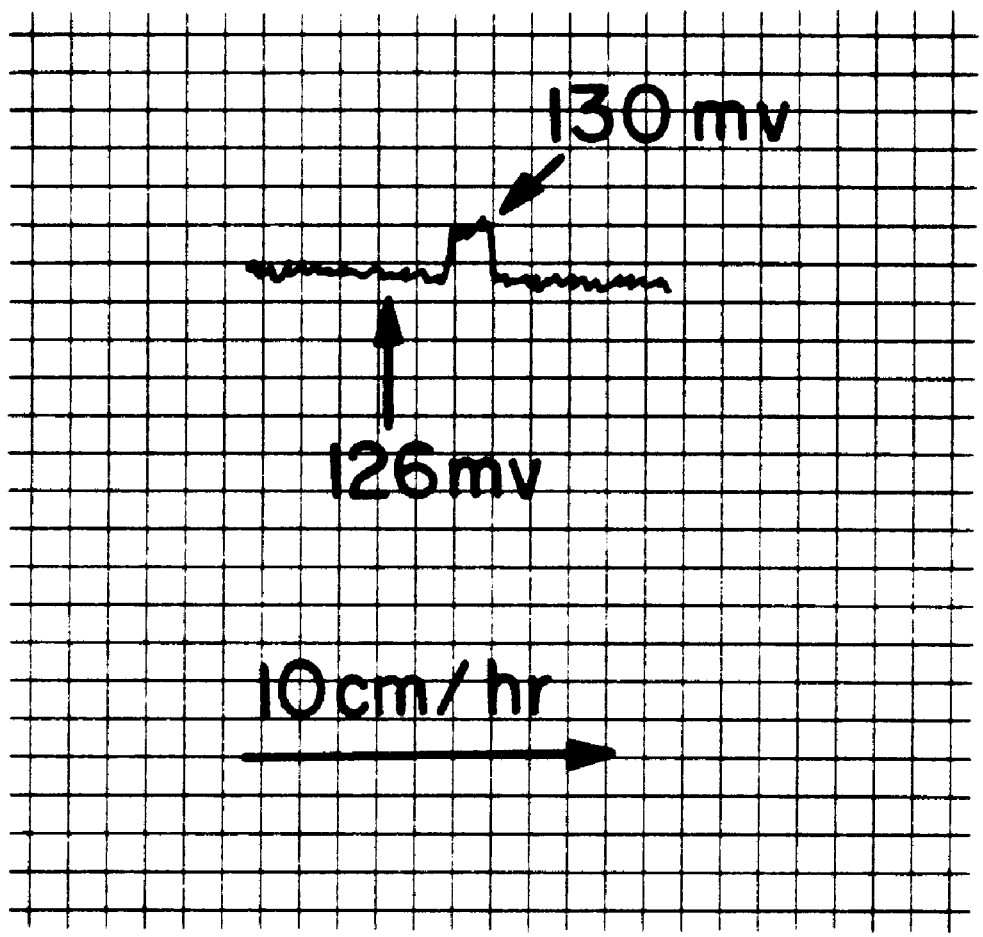
FIG. 16 is a graphical depiction of data from the first cell with no insert.

The baseline was established using pure argon at 126 mV with a slight downward drift during this run. One sample containing 250 ppb $H_2S$ in argon was introduced into the oxidation furnace and the resulting $SO_2$ produced about a 4 mV response peak as shown in FIG. 16, with the chart recorder run at 10 cm/hr. The results were similar to the results of example 1, except that the response was about half of the original value.

Examples 8

This example illustrates a retest of the cell of example 1 after cleaning, no insert.

Figure 17:
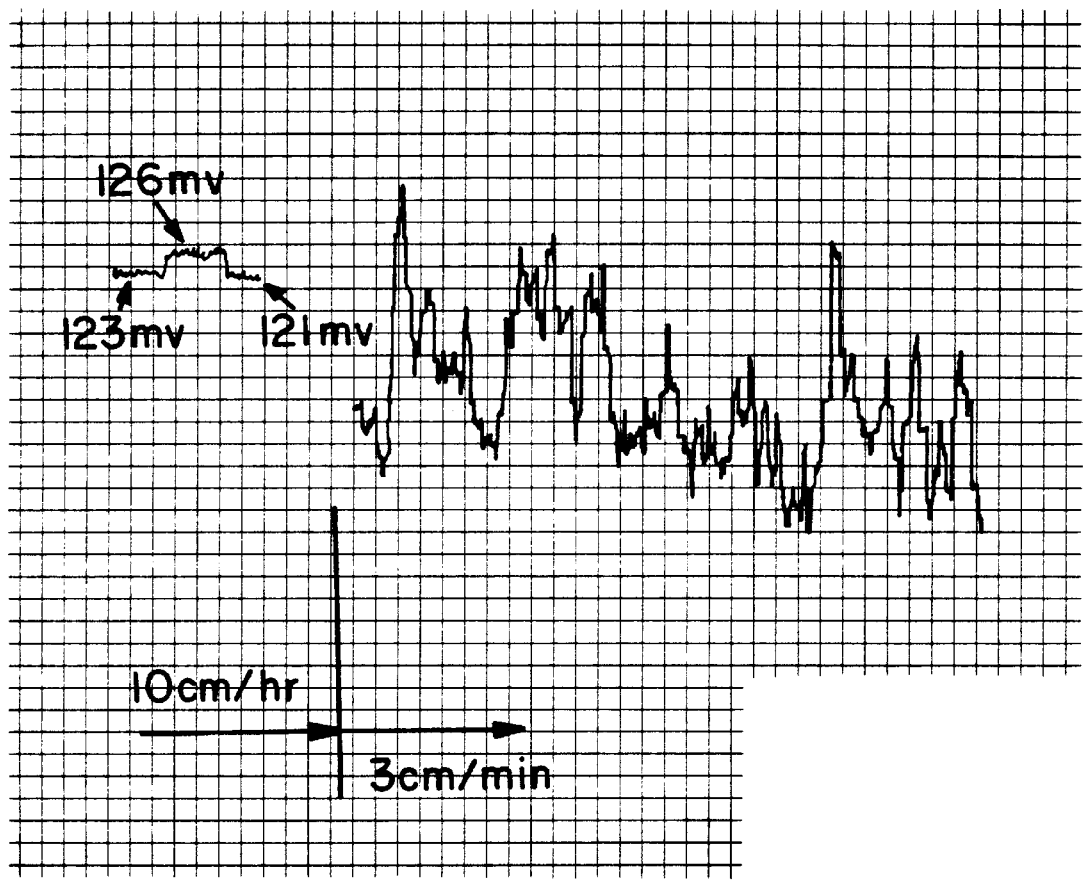
FIG. 17 is a graphical depiction of data from the first cell with no insert.

The baseline was established using pure argon at 123 mV with a slight downward drift during this run. One sample containing 250 ppb $H_2S$ in argon was introduced into the oxidation furnace and the resulting $SO_2$ produced about a 4 mV response peak as shown in FIG. 17, with the chart recorder run at 10 cm/hr. The chart recorder was then expanded 50 times, zeroed, centered, filtered with a 2 second RC filter and run at 3 cm/min to obtain a visual measure of baseline noise. The results were similar to the results of example 1, except that the response was about half of the original value. Note that the results of examples 7 and 8 are nearly identical.

Examples 9

This example illustrates a retest of the cell of example 3.

Figure 18:
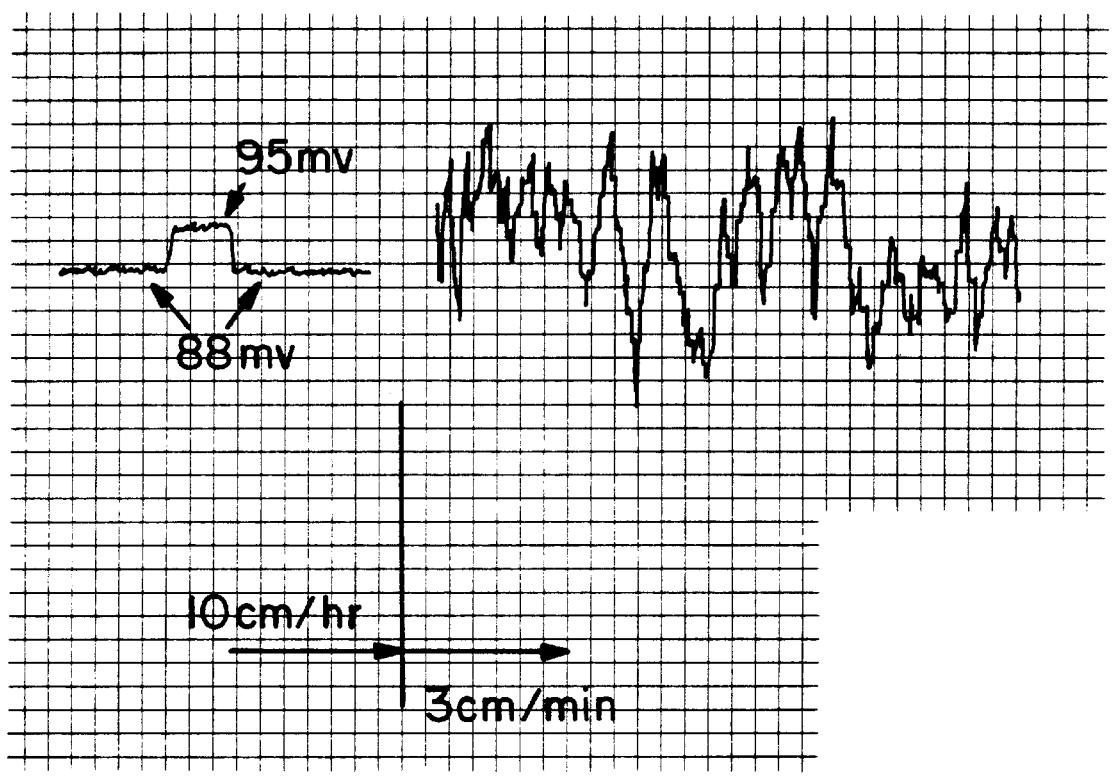
FIG. 18 is a graphical depiction of data from the first cell with an insert having a polished interior surface with barely visible lengthwise scratches.

The baseline was established using pure argon at 88 mV. One sample containing 250 ppb $H_2S$ in argon was introduced into the oxidation furnace and the resulting $SO_2$ produced a 7 mV response peaks as shown in FIG. 18, with the chart recorder run at 10 cm/hr. The results were similar to the results of example 3.

Examples 10

This example illustrates the baseline, response and noise of the first fluorescent detector cell to 250 ppb $H_2S$ in argon where the detector cell includes a second circularly polished insert having barely visible scratches on the circumference of the insert.

Figure 19:
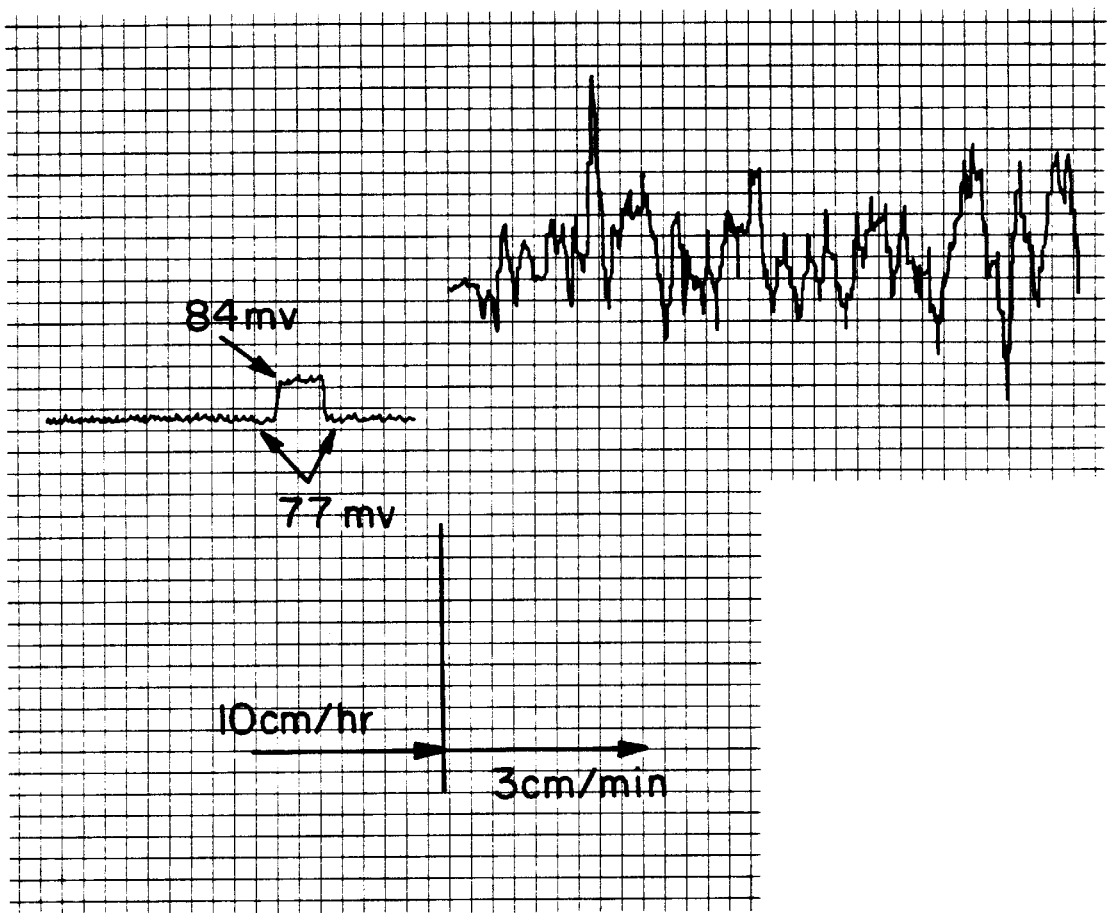
FIG. 19 is a graphical depiction of data from the first cell with another insert having a polished interior surface with barely visible lengthwise scratches.

The baseline was established using pure argon at 77 mV. One sample containing 250 ppb $H_2S$ in argon was introduced into the oxidation furnace and the resulting $SO_2$ produced about a 7 mV response peaks as shown in FIG. 19, with the chart recorder run at 10 cm/hr. The chart recorder was then expanded 50 times, zeroed, centered, filtered with a 2 second RC filter and run at 3 cm/min to obtain a visual measure of baseline noise. The results were similar to the results of examples 3, 5, and 9 and are considerably better than the results of examples 1, 2, 4 7 and 8.

Examples 11

This example illustrates the baseline, response and noise of the first fluorescent detector cell to 250 ppb $H_2S$ in argon where the detector cell includes a third highly polished insert having an interior surface with barely visible scratches running the length of the insert.

Figure 20:
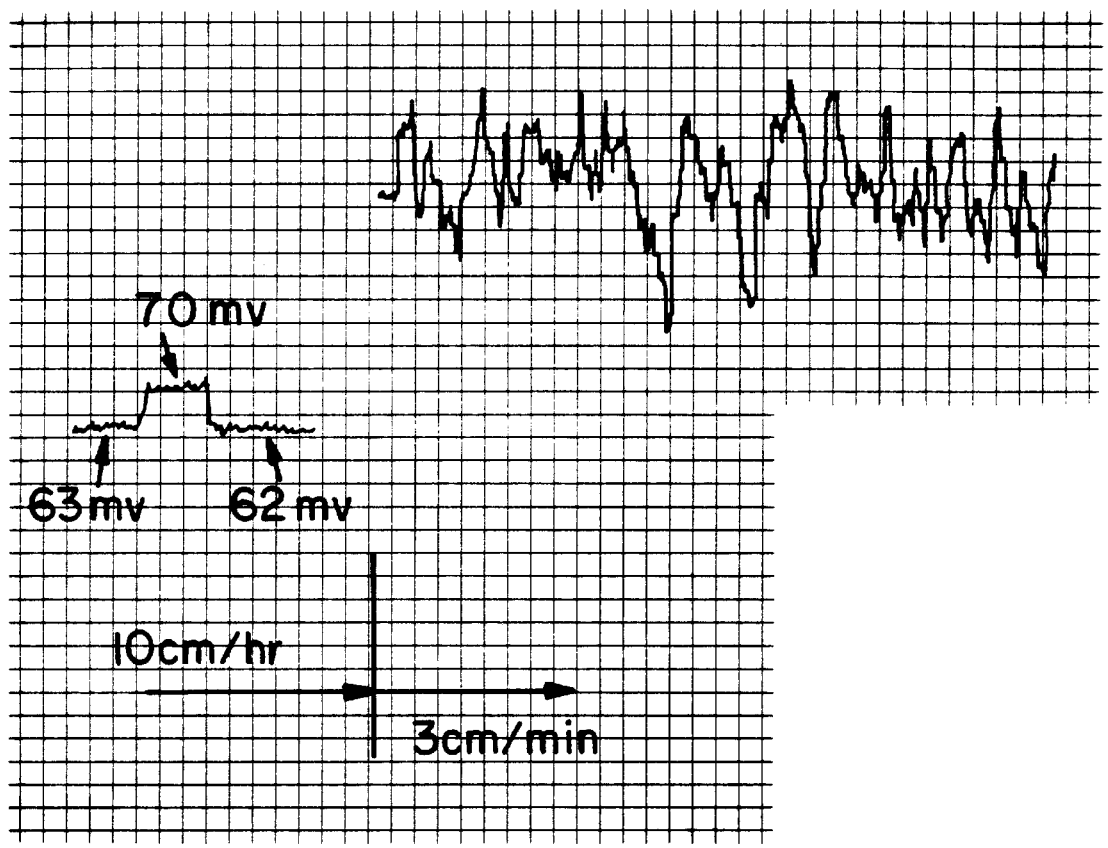
FIG. 20 is a graphical depiction of data from the first cell with a brass insert having a polished interior surface.

The baseline was established using pure argon at 62 mV with a slight downward drift during this run. One sample containing 250 ppb $H_2S$ in argon was introduced into the oxidation furnace and the resulting $SO_2$ produced about a 8 mV response peaks as shown in FIG. 20, with the chart recorder run at 10 cm/hr. The chart recorder was then expanded 50 times, zeroed, centered, filtered with a 2 second RC filter and run at 3 cm/min to obtain a visual measure of baseline noise. The results were similar to the results of examples 3, 5, 9 and 10 and are considerably better than the results of examples 1, 2, 4 7 and 8.

Examples 12

This example illustrates the baseline, response and noise of the first fluorescent detector cell to 250 ppb $H_2S$ in argon where the detector cell includes a cylindrical insert having an interior surface that was sand blasted and scratched lengthwise with #36 sandpaper and cleaned.

Figure 21:
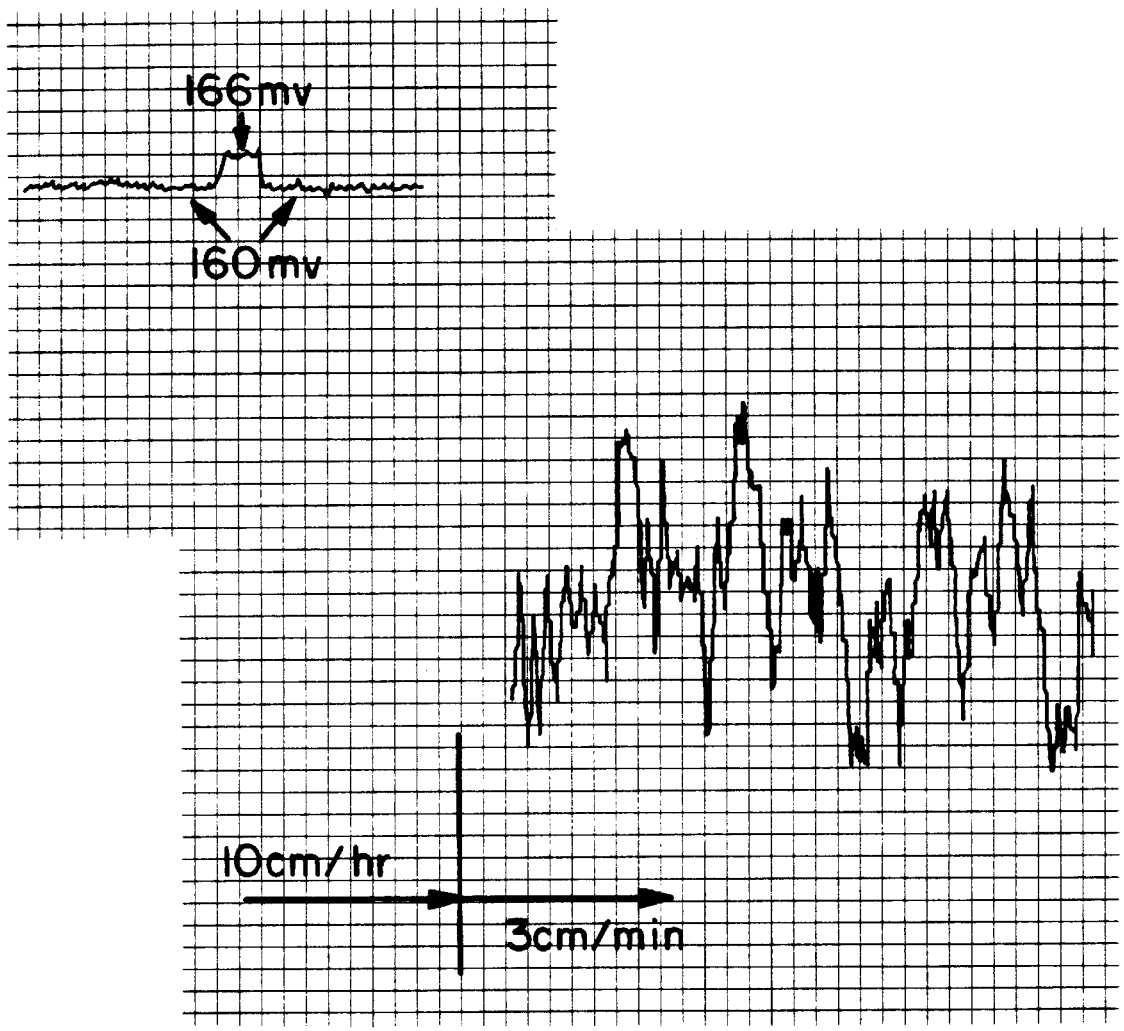
FIG. 21 is a graphical depiction of data from the first cell with an insert having a sand blasted interior surface with lengthwise scratched made by #36 sandpaper.

The baseline was established using pure argon at 160 mV. One sample containing 250 ppb $H_2S$ in argon was introduced into the oxidation furnace and the resulting $SO_2$ produced about a 6 mV response peaks as shown in FIG. 21, with the chart recorder run at 10 cm/hr. The chart recorder was then expanded 50 times, and run at 3 cm/min zeroed, centered, filtered with a 2 second RC filter to obtain a visual measure of baseline noise. The results were similar to the results of examples 3, 5, 9 and 10 and are considerably better than the results of examples 1, 2, 4 7 and 8.

Examples 13

This example illustrates the baseline, response and noise of the first fluorescent detector cell to 250 ppb $H_2S$ in argon where the detector cell includes a cylindrical insert having an unpolished interior surface with deep circular scratches.

Figure 22:
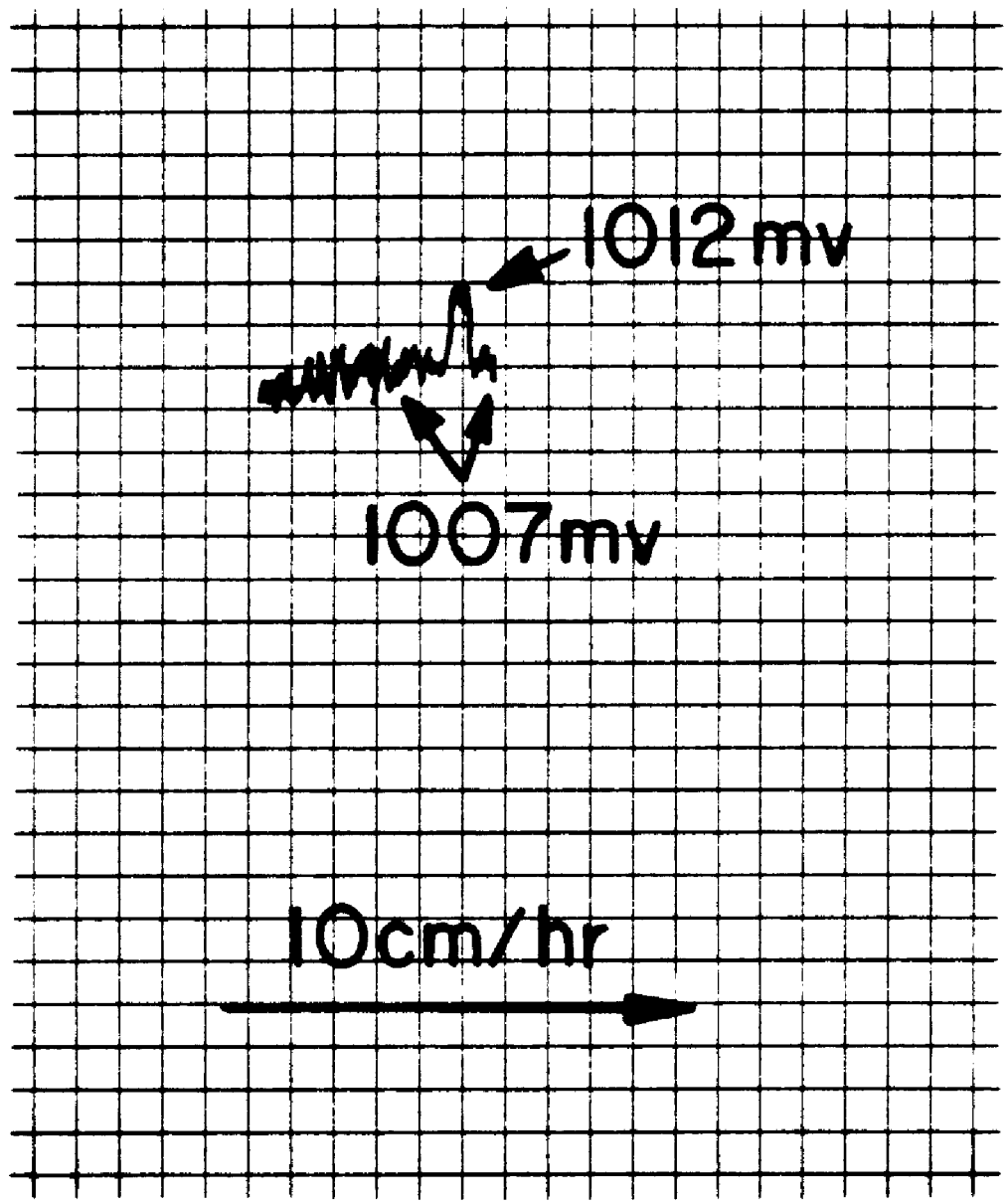
FIG. 22 is a graphical depiction of data from the first cell with an insert having an unpolished interior surface with deep radial scratches.

The baseline was established using pure argon at 1007 mV. The raw signal bucked on scale with a multivolt supply. One sample containing 250 ppb $H_2S$ in argon was introduced into the oxidation furnace and the resulting $SO_2$ produced about a 5 mV response peaks as shown in FIG. 22. Because the baseline response was difficult to keep on the chart, no expanded scale data was taken. But, the thickness of the baseline is evidence of considerable noise in the baseline signal and the response signal.

Examples 14

This example illustrates is a retest of the cell of examples 1, 7 and 8 with no insert.

Figure 23:
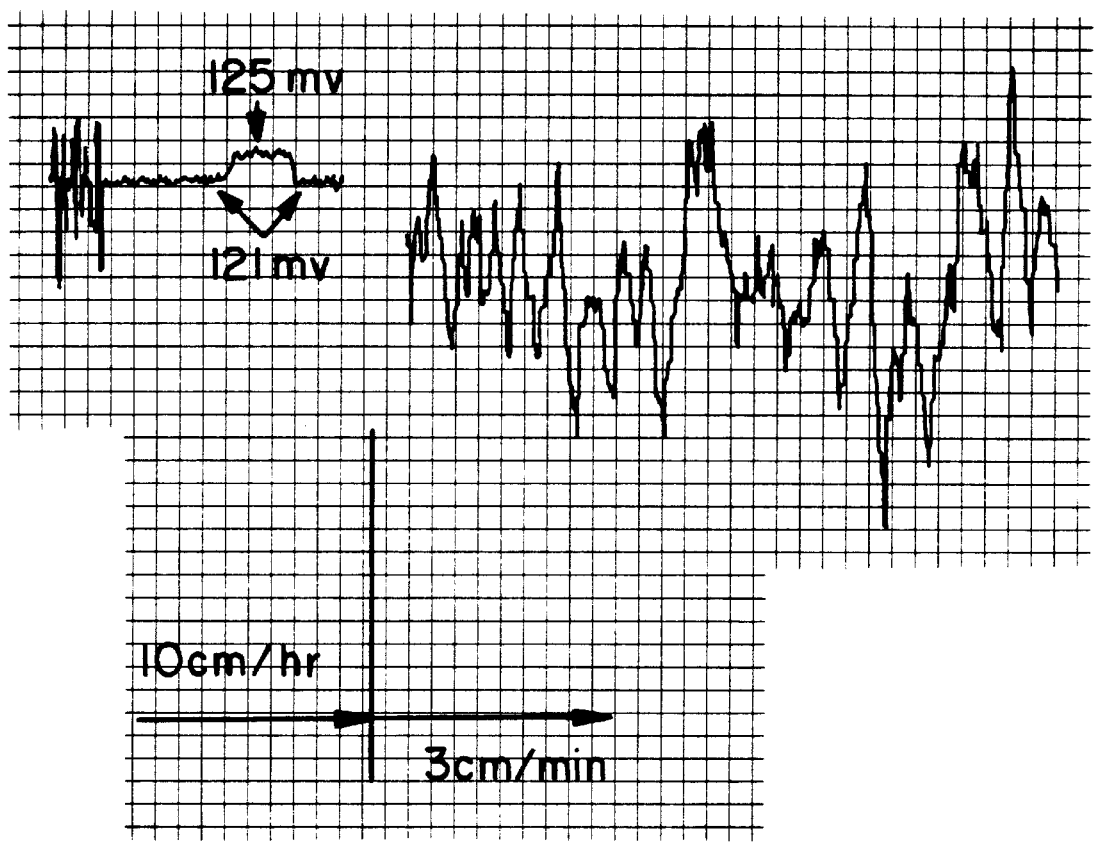
FIG. 23 is a graphical depiction of data from the first cell with no insert.

The baseline was established using pure argon at 121 mV. One sample containing 250 ppb $H_2S$ in argon was introduced into the oxidation furnace and the resulting $SO_2$ produced about a 4 mV response peaks as shown in FIG. 23, with the chart recorder run at 10 cm/hr. The chart recorder was then expanded 50 times, zeroed, centered, filtered with a 2 second RC filter and run at 3 cm/min to obtain a visual measure of baseline noise. The results were similar to the results of examples 1, 7 and 8.

Examples 15

This example illustrates the baseline, response and noise of a second fluorescent detector cell to 250 ppb $H_2S$ in argon where detector cell has no insert.

Figure 24:
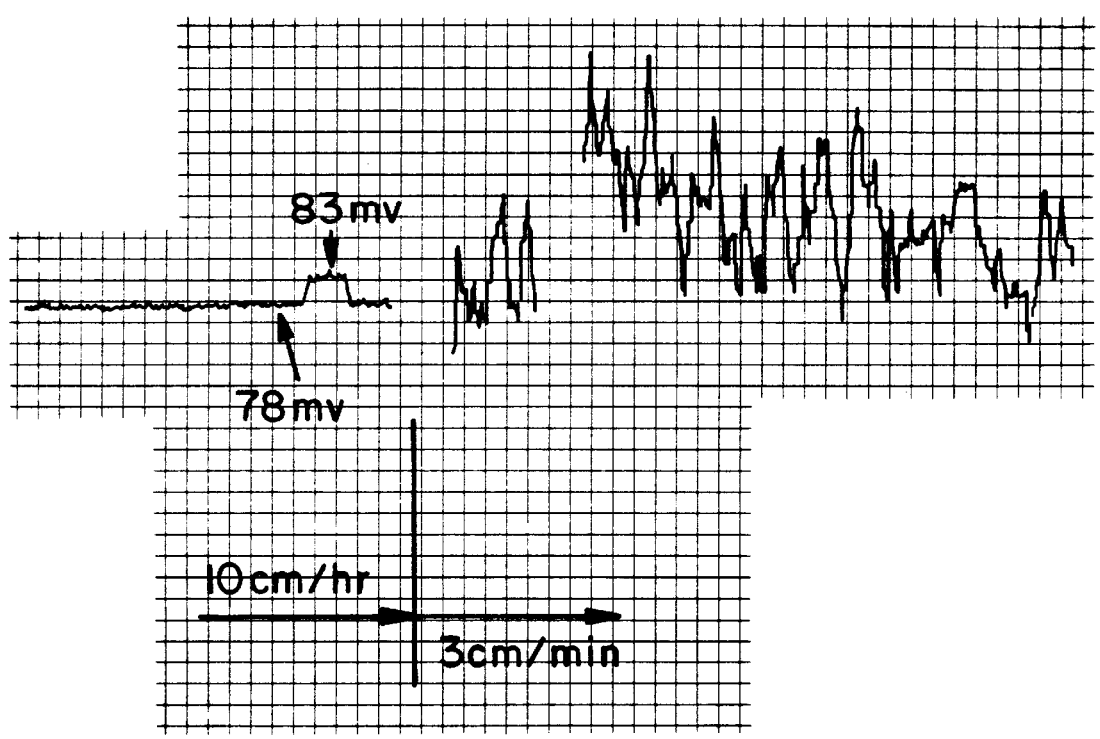
FIG. 24 is a graphical depiction of data from a second cell with no insert.

The baseline was established using pure argon at 78 mV. One sample containing 250 ppb $H_2S$ in argon was introduced into the oxidation furnace and the resulting $SO_2$ produced about a 5 mV response peaks as shown in FIG. 24, with the chart recorder run at 10 cm/hr. The chart recorder was then expanded 50 times, zeroed, centered, filtered with a 2 second RC filter and run at 3 cm/min to obtain a visual measure of baseline noise. The results were similar to the results of examples 7 and 8 using the first cell.

Examples 16

This example illustrates the baseline, response and noise of the second fluorescent detector cell to 250 ppb $H_2S$ in argon where the detector cell includes a cylindrical insert having a polished interior surface with barely visible scratches oriented along the length of the insert.

Figure 25:
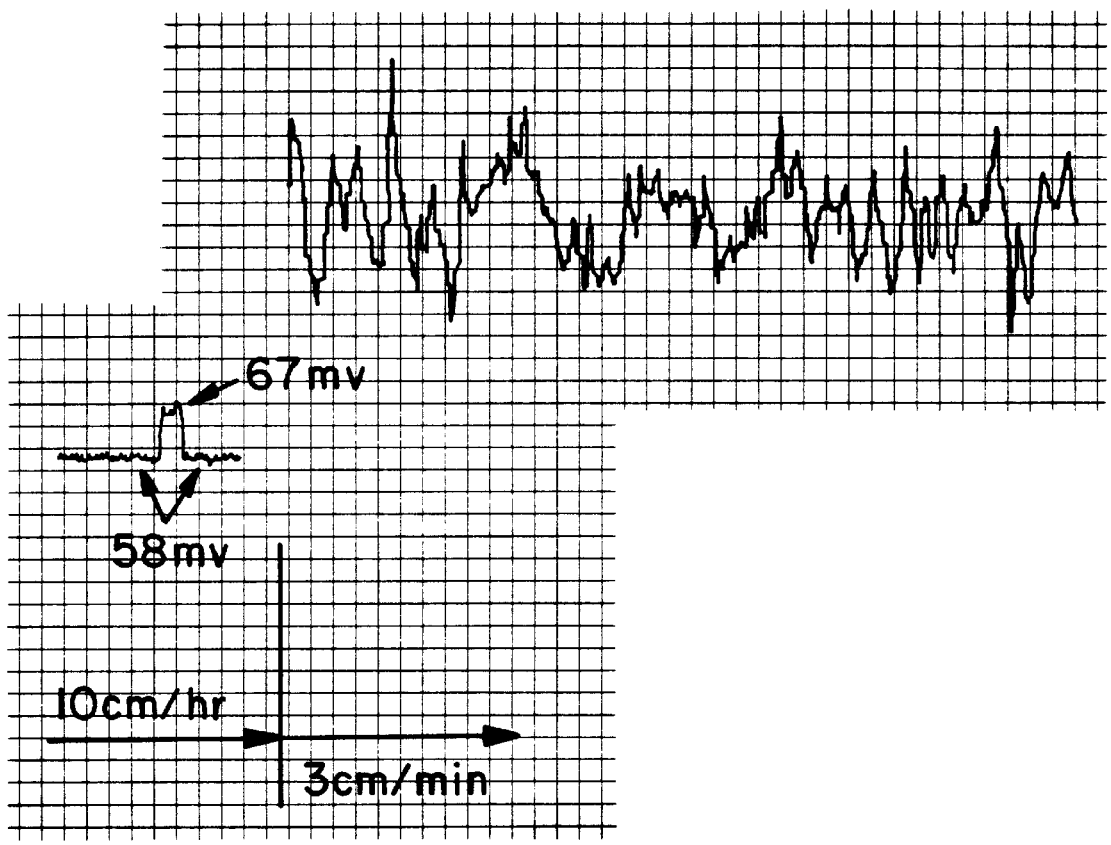
FIG. 25 is a graphical depiction of data from the second cell with an insert having a polished interior surface with barely visible lengthwise scratches.

The baseline was established using pure argon at 58 mV. One sample containing 250 ppb $H_2S$ in argon was introduced into the oxidation furnace and the resulting $SO_2$ produced about a 9 mV response peaks as shown in FIG. 25, with the chart recorder run at 10 cm/hr. The chart recorder was then expanded 50 times, zeroed, centered, filtered with a 2 second RC filter and run at 3 cm/min to obtain a visual measure of baseline noise. The results show better response sensitivity and better signal-to-noise than for the cell without insert per example 15.

Examples 17

This example illustrates the baseline, response and noise of the second fluorescent detector cell to 250 ppb $H_2S$ in argon where the detector cell includes a cylindrical brass, rhodium plated interior surface that was highly polished prior to plating. The interior surface was highly reflective and smooth.

Figure 26:
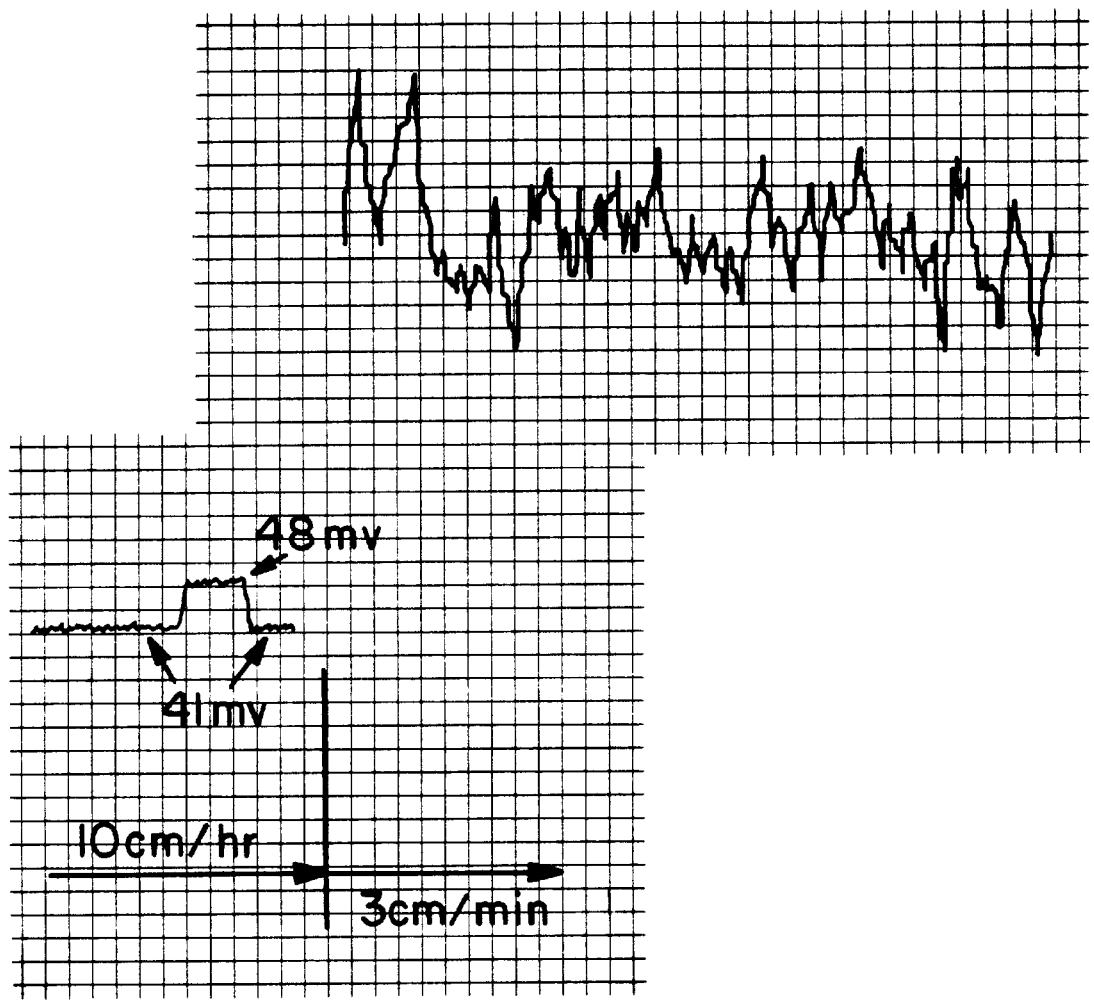
FIG. 26 is a graphical depiction of data from the second cell with a brass insert having rhodium plated interior surface.

The baseline was established using pure argon at 41 mV. One sample containing 250 ppb $H_2S$ in argon was introduced into the oxidation furnace and the resulting $SO_2$ produced about a 7 mV response peaks as shown in FIG. 26, with the chart recorder run at 10 cm/hr. The chart recorder was then expanded 50 times, zeroed, centered, filtered with a 2 second RC filter and run at 3 cm/min to obtain a visual measure of baseline noise. The results show better response sensitivity and better signal-to-noise than for the cell without insert per example 15 and are similar to the results of example 16.

Examples 18

This example illustrates the baseline, response and noise of a fluorescent detector cell to 250 ppb $H_2S$ in argon where the detector cell includes a cylindrical insert having an interior surface that was sand blasted and scratched lengthwise with #36 sandpaper and cleaned.

Figure 27:
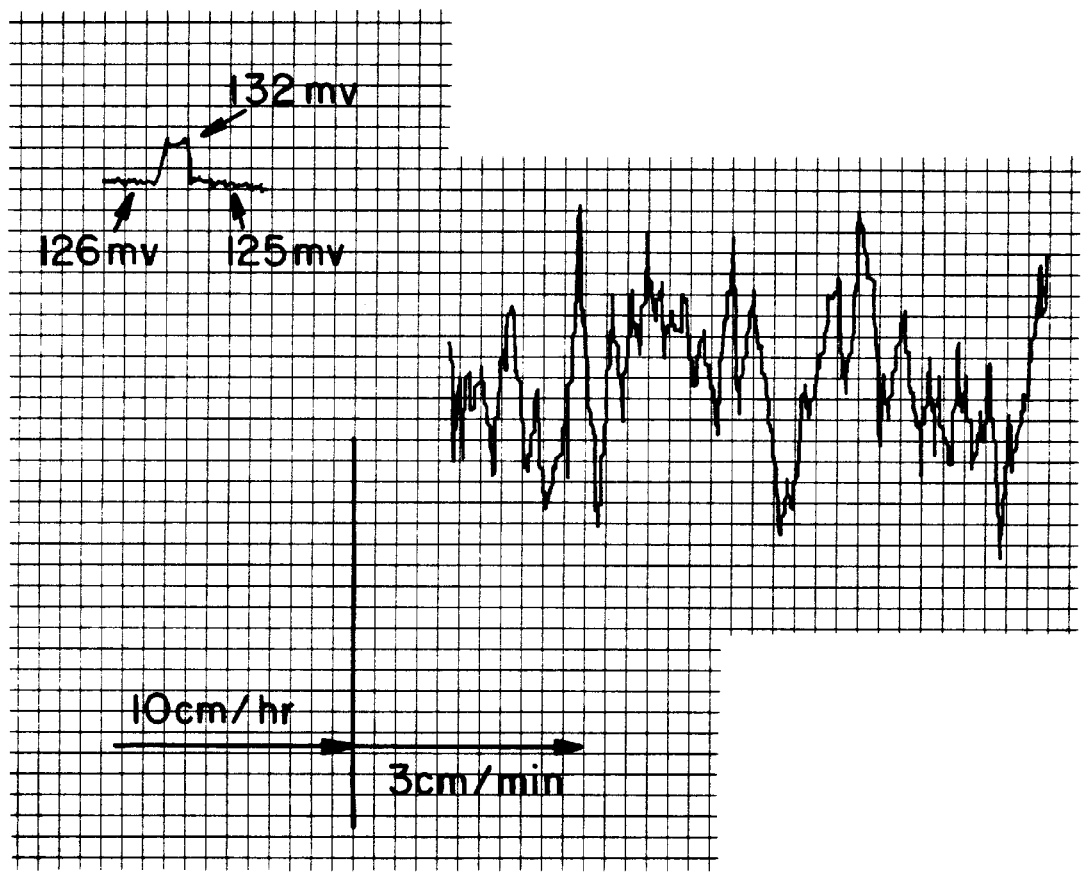
FIG. 27 is a graphical depiction of data from the second cell with an insert having a sand blasted interior surface with lengthwise scratches from #36 sandpaper.

The baseline was established using pure argon at 126 mV with a downward drift during this run. The chart recorder was zero off set negative to get signal on chart. One sample containing 250 ppb $H_2S$ in argon was introduced into the oxidation furnace and the resulting $SO_2$ produced about a 6 mV response peaks as shown in FIG. 27, with the chart recorder run at 10 cm/hr. The chart recorder was then expanded 50 times, zeroed, centered, filtered with a 2 second RC filter and run at 3 cm/min to obtain a visual measure of baseline noise. The results were similar to the results of example 15.

Looking at the results of the comparative testing of fluorescent cells with and without insert and with and without highly polished inserts, it is qualitatively apparent at inserts with highly polished interior surfaces improve sensitivity (response height to baseline value) and greatly improve baseline noise.

Although the invention has been disclosed with reference to its preferred embodiments, from reading this description those of skill in the art may appreciate changes and modifications that may be made which do not depart from the scope and spirit of the invention as described above and claimed hereafter.

We claim:

1. A reaction cell comprising:

a body;

an interior light excitation chamber adapted to receive a sample and excitation light;

an excitation light inlet positioned at one end of the body through which the excitation light enters the chamber;

an fluorescent light outlet oriented substantially perpendicular to the excitation light inlet through which fluorescent light leaves the chamber;

a sample inlet through which the sample enters the chamber;

a sample outlet through which the sample leaves the interior of the chamber; and a portion of an interior surface of the chamber having a rms smoothness less than or equal to $200\mu"$ and a reflectance of at least 70% for the fluorescent light, where a portion of reflected fluorescent light strikes the portion of the surface and passes through the fluorescent light outlet.

2. The cell of claim 1, wherein the rms smoothness is less than or equal to $10\mu"$ and the reflectance is at least 90%.

3. The cell of claim 1, wherein the rms smoothness is between $0.1\mu"$ and $10\mu"$ and the reflectance is at least 95%.

4. A reaction cell comprising:

a body;

an interior light excitation chamber adapted to receive a sample and excitation light;

an excitation light inlet positioned at one end of the chamber through which the excitation light enters the chamber;

an fluorescent light outlet oriented substantially perpendicular to the excitation light inlet through which fluorescent light leaves the chamber;

a sample inlet through which the sample enters the chamber;

a sample outlet through which the sample leaves the chamber; and an insert conforming substantially to the chamber including a portion of an inner surface of the insert having a rms smoothness less than or equal to $200\mu"$ and a reflectance of at least 70% for the fluorescent light, where a portion of reflected fluorescent light strikes the portion of the surface and passes through the fluorescent light outlet.

5. The cell of claim 4, wherein the rms smoothness is less than or equal to $10\mu"$ and the reflectance is at least 90%.

6. The cell of claim 4, wherein the rms smoothness between $0.1\mu"$ and $10\mu"$ and the reflectance is at least 95%.

7. A light excitation chamber insert comprising a hollow member including an excitation light inlet, a fluorescent light outlet oriented substantially perpendicular to the excitation light inlet, a sample inlet, a sample outlet and an interior surface having a rms smoothness less than or equal to $200\mu"$ and a reflectance of at least 70% to a frequency range corresponding to fluorescent light to be detected, where the insert is designed to reflect a portion of fluorescent light into the fluorescent light outlet.

8. The insert of claim 7, wherein the rms smoothness is less than or equal to $10\mu"$ and the reflectance is at least 90%, the sample inlet orifice is an alignment slot and insert substantially conforms to an interior of a hollow reaction cell.

9. The insert of claim 7, wherein the rms smoothness between $0.1\mu"$ and $10\mu"$ and the reflectance is at least 95%, the sample inlet orifice is an alignment slot and insert substantially conforms to an interior of a hollow reaction cell.

10. A reaction cell comprising:

an interior chamber including an interior surface having a rms smoothness less than or equal to $200\mu"$ and a reflectance of at least 70% to a fluorescent light frequency range;

an excitation light port positioned at one end of the cell and adapted to be placed in optical communication with an excitation light source for supplying excitation light into the chamber;

a sample inlet port for supplying a sample into the chamber so that a portion of a sample interacts with the excitation light to form excited species;

a fluorescent light detector port adapted to be in optical communication with a fluorescent light detector for detecting; and a sample outlet port providing an exit for the sample out of the chamber; where a first portion of fluorescent light passes directly through the detector port and a second portion of fluorescent light is reflected by the interior surface of the chamber and passes through the detector port.

11. The cell of claim 10, wherein the rms smoothness is less than or equal to $10\mu"$ and the reflectance is at least 90%.

12. The cell of claim 10, wherein the rms smoothness between $0.1\mu"$ and $10\mu"$ and the reflectance is at least 95%.

13. An apparatus comprising:
   a. a sample supply component;
   b. an excitation light source component for generating excitation light in a given excitation frequency range;
   c. a light reaction cell comprising:
      i. a body;
      ii. an interior light excitation chamber adapted to receive a sample and excitation light;
      iii. an excitation light inlet positioned at one end of the body through which the excitation light enters the chamber;
      iv. an fluorescent light outlet oriented substantially perpendicular to the excitation light inlet through which fluorescent light leaves the chamber;
      v. a sample inlet through which the sample enters the chamber;
      vi. a sample outlet through which the sample leaves the interior of the chamber; and
      vii. a portion of an interior surface of the chamber having a rms smoothness less than or equal to $200\mu"$ and a reflectance of at least 70% for the fluorescent light, where a portion of reflected fluorescent light strikes the portion of the surface and passes through the fluorescent light outlet;
   d. a fluorescent light detector component in optical communication with the chamber of the cell for detecting a first portion of fluorescent light emitted directly by the excited species into the detector and a second portion of fluorescent light emitted by the excited species and reflected by the interior surface of the chamber into the detector; and
   e. a signal analyzing component, in electrical communication with the fluorescent detector component, for converting a detector output signal into quantified concentrations of the excited species.

14. The apparatus of claim 13, wherein the rms smoothness is less than $10\mu"$ and the reflectance is at least 90%.

15. The apparatus of claim 13, wherein the rms smoothness between $0.1\mu"$ and $10\mu"$ and the reflectance is at least 95%.

16. An apparatus comprising:
   a. a sample supply component for supplying a sample;
   b. a sample conversion component in fluid communication with the sample supply component for converting a portion of the sample into light excitable species;
   c. an excitation light source component for generating excitation light of an excitation frequency range;
   d. a light reaction cell comprising:
      i. a body;
      ii. an interior light excitation chamber adapted to receive a sample and excitation light;
      iii. an excitation light inlet positioned at one end of the body through which the excitation light enters the chamber;
      iv. an fluorescent light outlet oriented substantially perpendicular to the excitation light inlet through which fluorescent light leaves the chamber;
      V. a sample inlet through which the sample enters the chamber;
      vi. a sample outlet through which the sample leaves the interior of the chamber; and
      vii. a portion of an interior surface of the chamber having a rms smoothness less than or equal to $200\mu"$ and a reflectance of at least 70% for the fluorescent light, where a portion of reflected fluorescent light strikes the portion of the surface and passes through the fluorescent light outlet;
   e. a fluorescent light detector component in optical communication with the chamber of the cell for detecting a first portion of fluorescent light emitted directly by the excited species into the detector and a second portion of fluorescent light emitted by the excited species and reflected by the interior surface of the chamber into the detector;
   f. a signal analyzing component, in electrical communication with the fluorescent detector component, for converting a detector output signal into quantified concentrations of the excited species.

17. The apparatus of claim 16, wherein the rms smoothness is less than $10\mu"$ and the reflectance is at least 90%.

18. The apparatus of claim 16, wherein the rms smoothness between $0.1\mu"$ and $10\mu"$ and the reflectance is at least 95%.

19. The apparatus of claim 16, wherein the conversion component is an oxidation chamber.

20. The apparatus of claim 19, wherein the sample is oxidized in the oxidation chamber and wherein the excitable species are selected from the group consisting of oxides of nitrogen and sulfur in the presence of an oxidizing agent.

21. The apparatus of claim 20, wherein the oxidation chamber is heated to an elevated temperature.

22. The apparatus of claim 21, wherein the oxidizing agent is oxygen.

23. A method comprising the steps of:
   (a) exciting species capable of undergoing light induced fluorescence in a fluorescence frequency range with excitation light in an excitation frequency range to form excited species in a light reaction cell comprising:
      a body;
      an interior light excitation chamber adapted to receive a sample and excitation light;
      an excitation light inlet positioned at one end of the body through which the excitation light enters the chamber;
      an fluorescent light outlet oriented substantially perpendicular to the excitation light inlet through which fluorescent light leaves the chamber;
      a sample inlet through which the sample enters the chamber;
      a sample outlet through which the sample leaves the interior of the chamber; and
      a portion of an interior surface of the chamber having a rms smoothness less than or equal to $200\mu"$ and a reflectance of at least 70% for the fluorescent light, where a portion of reflected fluorescent light strikes the portion of the surface and passes through the fluorescent light outlet; and
   (b) detecting fluorescent light emitted by the excited species of step (b) in a fluorescent light detector where a first portion of fluorescent light is emitted directly by the excited species into the detector and a second portion of fluorescent light is emitted by the excited species and reflected by the interior surface of the chamber into the detector.

24. A method comprising the steps of:
(a) converting a portion of a sample into a detectable concentration of species capable of undergoing light induced fluorescence in a fluorescence frequency range;
(b) exciting a portion of the detectable species of step (a) with excitation light in an excitation frequency range to form excited species in a light reaction cell comprising:
   a body;
   an interior light excitation chamber adapted to receive a sample and excitation light;
   an excitation light inlet positioned at one end of the body through which the excitation light enters the chamber;
   an fluorescent light outlet oriented substantially perpendicular to the excitation light inlet through which fluorescent light leaves the chamber;
   a sample inlet through which the sample enters the chamber;
   a sample outlet through which the sample leaves the interior of the chamber; and
   a portion of an interior surface of the chamber having a rms smoothness less than or equal to $200\mu''$ and a reflectance of at least 70% for the fluorescent light, where a portion of reflected fluorescent light strikes the portion of the surface and passes through the fluorescent light outlet; and
(c) detecting fluorescent light emitted by the excited species of step (b) in the fluorescent light detector where a first portion of fluorescent light is emitted directly by the excited species into the detector and a second portion of fluorescent light is emitted by the excited species and reflected by the interior surface of the chamber into the detector.

* * * * *